United States Patent
Edwards et al.

US006469230B1

(10) Patent No.: US 6,469,230 B1
(45) Date of Patent: Oct. 22, 2002

(54) STARCH DEBRANCHING ENZYMES

(75) Inventors: Elizabeth Anne Edwards; Alison Mary Smith; Catherine Rosemary Martin; Regla Bustos Guillen, all of Norfolk (GB)

(73) Assignee: Plant Bioscience Limited, Norfolk (GB)

( * ) Notice: Subject to any disclaimer, the term of this patent is extended or adjusted under 35 U.S.C. 154(b) by 0 days.

(21) Appl. No.: 09/463,238

(22) PCT Filed: Jul. 30, 1998

(86) PCT No.: PCT/GB98/02280

§ 371 (c)(1),
(2), (4) Date: Jan. 21, 2000

(87) PCT Pub. No.: WO99/06575

PCT Pub. Date: Feb. 11, 1999

(30) Foreign Application Priority Data

Jul. 31, 1997 (GB) ............................................... 9716185

(51) Int. Cl.[7] ........................ C12N 15/29; C12N 15/56; C12N 15/82; C12N 5/04; A01H 5/00
(52) U.S. Cl. .................... 800/284; 800/278; 800/317.2; 800/320; 800/320.1; 800/320.2; 800/320.3; 536/23.6; 435/69.1; 435/210; 435/320.1; 435/419; 435/468
(58) Field of Search ..................... 536/23.6; 435/69.1, 435/210, 320.1, 419, 468; 800/278, 284, 317.2, 320, 320.1, 320.2, 320.3

(56) References Cited

U.S. PATENT DOCUMENTS

| | | |
|---|---|---|
| 5,527,898 A | 6/1996 | Bauer et al. |
| 5,614,619 A | 3/1997 | Piepersberg et al. |
| 5,750,876 A | 5/1998 | Barry et al. |
| 5,912,413 A | 6/1999 | Myers et al. |
| 6,255,563 B1 * | 7/2001 | Emmermann et al. ...... 800/284 |

FOREIGN PATENT DOCUMENTS

| | | |
|---|---|---|
| WO | WO92 11382 | 7/1992 |
| WO | WO95 04826 | 2/1995 |
| WO | WO96 03513 | 2/1996 |
| WO | WO96 19581 | 6/1996 |
| WO | WO 97/32985 | 9/1997 |
| WO | WO97 42328 | 11/1997 |
| WO | WO 98/50562 | 11/1998 |
| WO | WO 99/12950 | 3/1999 |
| WO | WO 99/58690 | 11/1999 |

OTHER PUBLICATIONS

Hannah et al. Scientia Horticultural 55: 177–197, 1993.*
Willmitzer et al. Plant Polymeric Carbohydrates, pp. 33–39, 1993.*
James, Martha G. et al., "Characterization of the Maize Gene sugaryl, a Determinant of Starch Composition in Kernels", The Plant Cell, 7: 417–429 (1995).
James, Martha G. et al., "Zea mays Sulp (Sugaryl) mRNA, partial cds.", EMBL Accession No. U18908, Apr. 19, 1995.
Database GENESEQ Accession No. Q51622, "6–o–methyldeoxyguanosine primer A", May 24, 1994.
Database GENESEQ Accession No. T44609, "Human papillomavirus detection probe MYB187 for HPV type 26", Jan. 28, 1997.
Ishizaki, Yukuo et al., "Debranching Enzymes of Potato Tubers (*Solanum tuberosum L.*), I. Purification and Some Properties of Potato Isoamylase", Agric. Biol. Chem., 47:771–779 (1983).
Kortstee, A.J. et al., "Expression of Escherichia coli branching enzyme in tubers of amylose–free transgenic potato leads to an increased branching degreee of the amylopectin", The Plant Journal, 10: 83–90 (1996).
Shewmaker, C.K. et al., "Expression of Escherichia Coli Glycogen Synthase in the Tubers of Transgenic Potatoes (Solanum Tuberosum) Results in a Highly Branched Starch", Plant Physiology, 104: 1159–1166 (1994).

* cited by examiner

*Primary Examiner*—David T. Fox
(74) *Attorney, Agent, or Firm*—Dann, Dorfman, Herrell and Skillman

(57) ABSTRACT

The invention relates to isolated nucleic acids obtainable from potato which encode isoamylases, a type of starch branching enzyme, particularly SEQ ID NOS:1–3 or variants encoding SEQ ID NOS:4–6; vectors comprising the nucleic acids; plant cells and plants transformed therewith; and methods for making plants which produce starches with modified branching characteristics.

20 Claims, 19 Drawing Sheets

Fig. 1A

```
   1  CTTATGGGAC TTGATTAAGA ATATGTGATC CACCAAGTTC TATATCTGAC
  51  GCTGTCGTAA CATTGTGTGC TGCTAATGGC AACTTCACCA ATACAGTTGG
 101  CTGTGCATTC ACGTTTGTTG AGCTATGGCA GTACTGAGTC AACCAAGTTG
 151  GTTCCTTCAT CATCAGGTAA CCGTGGAAAA ATAGTATGCA GTCTAAGGAA
 201  GCTGGAATTG GAAGACATGA ATTTCTCTGG CATAGGTCGA AATAATGATC
 251  AAGAAGCTCC TAGGAGAGCT CATCGACGAA AAGCACTATC AGCATCGAGA
 301  ATTTCGCTTG TTCCATCTGC AAAAAGGGTT CCCACTTACC TTTTCAGGAC
 351  AGATATTGGT GGTCAAGTGA AAGTCTTGGT GGAAAGGACA AATGGAAAGT
 401  ACAAAGTGCT TGTAGAAGTA TTGCCATTGG AGCTCTCATA TGCACATTCT
 451  GAGCTGGTTA TGGTTTGGGG TCTTTTTAGA TCTGATGCTT CATGCTTTAT
 501  GCCTCTAGAT CTAAATAGAC GTGGAGCAGA TGGAAAAAGT AGTACTGTTG
 551  AAACACCATT TGTGCAAGGA CCTTCAGGCA AGGTCACCGT GGAGCTGGAT
 601  TTTGAAGCAA GTTTAGCCCC CTTCTATATC TCCTTCTATA TGAAGTCGCA
 651  ACTAGTTTCT GACATGGAAA ACTCAGAAAT CAGAAGTCAC AGGAACACAA
 701  ATTTTGTTGT ACCAGTTGGT CTCAGTTCAG GGCATCCTGC TCCATTGGGT
 751  ATTTCCTTTC AGCCAGATGG ATCTGTGAAT TTTGCTCTCT TCTCACGCAG
 801  TGCAAGAAGT GTAGTTCTGT GCTTGTATGA TGACATATCA GTTGAAAAAC
 851  CTTCTTTAGA GATTGATCTA GATCCTTATA TTAATCGATC AGGCGATATT
 901  TGGCATGCTG CTTTAGATTG TTCTTTGCCA TTTAAGACTT ATGGTTATAG
 951  ATGTAAGGCG ACTACTTCTG GGAAGGGAGA GCTGGTTCTT TTGGACCCAT
1001  ATGCTAAGGT GATAAGGCGT GTTATTCCTC GTCAGGGTGG GTCTGAGATA
1051  CGTCCAAAAT ATCTTGGAGA ACTATGCCTG GAACCTGGCT ATGATTGGAG
1101  CGGTGATGTC CCCCCTAGCT TACCTATGGA GAAACTAATA ATTTACCGCT
1151  TAAATGTGAC TCAATTTACA AAGGACAAGT CCAGTAAGCT ACCTGATGAC
1201  CTTGCTGGAA CTTTCTCTGG CATTAGCGAA AAATGGCACC ATTTTAAAGA
1251  TCTTGGTGTG AATGCAATGT TACTGGAGCC AATTTTCCCT TTTGATGAGC
1301  AGAAAGGACC CTATTTTCCG TGGCATTTCT TCTCACCTGG AAATATGTAT
1351  GGACCTTCTG GTGACCCTCT TTCTGCCATT AAATCGATGA AGGATATGGT
1401  TAAGAAATTA CATGCTAACG GGATAGAGGT TTTTCTTGAA GTTGTTTTCA
1451  CTCACACTGC AGAGGATGCA CCTTTGATGA ATGTTGATAA CTTTTCATAT
1501  TGCATAAAAG GTGGTCAGTA TCTGAATATT CAAAATGCAT TGAATTGCAA
```

```
1551  TTACCCCATA GTCCAACAAA TGATTTTGGA CTGTCTCCGC CACTGGGTAA
1601  TTGAGTTTCA TATTGATGGT TTTGTTTTTG TCAACGCTTC TTCCTTGTTG
1651  AGAGGGTTCA ATGGAGAGAT TCTATCTCGT CCTCCATTAG TTGAAGCTAT
1701  TGCCTTTGAT CCTATCCTTT CAAAGGTCAA GATGATTGCA GATAATTGGA
1751  ATCCATTAAC CAATGATTCG AAGGAAAATT TATTCCCTCA CTGGAGGAGA
1801  TGGGCAGAGA TAAATATGAG ATTTTGTGAT GACATTCGAG ACTTCTTGAG
1851  AGGCGAGGGT CTTCTAAGCA ATCTAGCAAC ACGACTTTGT GGAAGTGGGG
1901  ATATCTTCGC AGGTGGACGT GGTCCTGCAT TCTCTTTTAA TTATATTGCC
1951  AGAAATTCTG GACTCACACT TGTTGACCTA GTTAGCTTCA GTAGTAATGA
2001  AGTGGCTTCA GAGTTAAGTT GGAACTGTGG ACAAGAAGGC GCTACGACCA
2051  ATAACATTGT CCTAGAGAGA CGACTTAAAC AAGTTCGTAA TTTTCTGTTC
2101  ATATTGTTCA TTTCTCTAGG TGTACCAGTA CTTAACATGG GAGACGAGTG
2151  TGGTCAGTCT TCAGGAGGTC CCCTGCATA TGATGCTCGA AAATCTTTGG
2201  GTTGGAATAC TTTAAAAACT GGTTTTGGGA CTCAGATTGC CCAGTTTATT
2251  TCATTCTTGA GTAATTTAAG AATGAGAAGA AGTGATCTTC TTCAAAAGAG
2301  AACCTTCTTG AAGGAAGAAA ACATCCAGTG GCATGGGAGT GACCAATCTC
2351  CTCCGAAATG GGATGGCCCG TCTAGCAAAT TCTTGGCTAT GACTTTGAAG
2401  GCCGATGCTG AAGTCAGCCA GACATTAGTC TCTGATATCG TAGGTGACCT
2451  GTTTGTTGCT TTCAATGGTG CTGGTGATTC AGAGATTGTT ATCCTTCCAC
2501  CTCCTCCAAC AGATATGGTA TGGCATCGTC TCGTTGACAC AGCCCTCCCT
2551  TTCCCGGGGT TTTTCGATGA GAAGGGAACT CCAGTTGAAG ATGAATTAGT
2601  TGCTTATGAG ATGAAGTCTC ACAGCTGTTT GCTGTTTGAA GCTCAGAGAC
2651  TAGCTGAAAT AGATTCTAGC AAGAGAAAGA AACAGATTAG ACTTTCTTCT
2701  AAGAGGCAAT AGTTTGTAAA GCCCCTAAGT ATATATATAT GTTTAAATAA
2751  GAGGCTTTTT TTTCTGAATA AATAAGAAGA TTTTACTGAG AATACTTGTA
2801  TCTAAACATT TTCTTTTGCA GCTTCAAATA AAAAAAAAAA AAA
```

```
   1  CTCAGTCCTT CTCAATTTCA GTGCCACATA CTCTAGATCA CACTCTCTCT
  51  TCTTCCTCAA AGTTCTCCCA TGGAGTTACT TCATTGTCCT TCCATTTCTA
 101  CCTACAAACC TAAACTCTCT TTCCACAACC ATCTTTTCTC GAGGAGAAGC
 151  AGTAACGGTG TAGATTTTGA GAGTATTTGG AGAAAATCGA GGTCTTCAGT
 201  GGTTAATGCT GCTGTTGATA GTGGACGTGG AGGTGTGGTG AAGACTGCGG
 251  CTACTGCGGT GGTGGTGGAG AAGCCGACGA CGGAACGATG TCGTTTTGAG
 301  GTTTTATCAG GGAAGCCATT GCCGTTTGGT GCTACTGCGA CAGATGGTGG
 351  TGTGAATTTC GCTGTTTTTT CAAGGAATGC TACAGCTGCT ACTCTTTGCT
 401  TGATCACTCT TTCCGATTTA CCTGAGAAGA GAGTGACCGA GCAAATTTTC
 451  CTGGATCCTC TAGCTAATAA AACTGGAGAT GTATGGCATG TGTTCCTTAA
 501  GGGAGATTTT GAGAATATGC TATATGGCTA CAAATTTGAT GGGAAATTCT
 551  GTCCTGAAGA AGGACACTAC TTTGACTCTT CGCAGATAGT GTTGGATCCT
 601  TATGCCAAGG CTATAGTAAG CAGAGGAGAA TATGGTGTAT TAGGGCCAGA
 651  GGATGATTGT TGGCCCCCAA TGGCTGGCAT GGTACCTTCT GCTTCTGATC
 701  AGTTTGATTG GAAGGAGAT CTACCACTGA AGTTTCCACA GAGAGATCTT
 751  GTAATCTATG AAATGCATGT TCGTGGGTTT ACTAATCATG AGTCGAGTGA
 801  AACAAAATAT CCTGGTACTT ACCTTGGTGT TGTGGAGAAA CTTGATCACT
 851  TGAAGGAACT TGGTGTCAAC TGTATAGAGC TAATGCCCTG TCACGAGTTC
 901  AATGAGCTGG AGTACTATAG TTATAACTCT GTATTGGGCG ACTACAAGTT
 951  TAACTTTTGG GGCTATTCTA CTGTCAATTT CTTTTCTCCA ATGGGAAGAT
1001  ACTCATCTGC TGGTCTAAGT AATTGCGGCC TCGGTGCAAT AAACGAATTT
1051  AAGTATCTTG TCAAGGAAGC ACATAAACGT GGAATCGAGG TTATCATGGA
1101  TGTTGTTTTC AATCACACTG CTGAAGGAAA TGAAAATGGT CCCATACTAT
1151  CATTTAGAGG CATTGACAAC AGTGTGTTTT ATACGCTAGC TCCTAAGGGT
1201  GAATTTTACA ACTACTCAGG ATGTGGAAAT ACCTTCAACT GTAATAATCC
1251  CATTGTACGT CAATTTATAG TGGATTGCTT GAGATATTGG GTTACCGAAA
1301  TGCACGTAgA TGGCTTCCGC TTTGATCTTG CTTCTATCCT TACAAGAAGT
1351  AGCAGCTCGT GGAATGCTGT AAATGTCTAT GGAAATTCAA TTGACGGTGA
1401  CGTGATCaCC ACAGGCACTC CTCTCACAAG CCCACCATTG ATTGATATGA
1451  TTAGCAATGA TCCAATACTT CGTGGAGTAA AGCTTATAGC TGAAGCATGG
1501  GATTGTGGAG GCCTTTACCA AGTTGGCATG TTTCCGCACT GGGGTATCTG
```

1551 GTCGGAGTGG AACGGAAAGT ACCGTGACAT GGTACGGCAG TTCATCAAAG

1601 GCACTGATGG GTTTTCTGGG GCTTTTGCTG AATGCCTTTG TGGAAGCCCA

1651 AATCTATACC AGAAAGGAGG AAGAAAACCA TGGAACAGTA TAAATTTCGT

1701 GTGTGCCCAC GATGGTTTTA CTTTGGCTGA TTTAGTGACA TACAACAATA

1751 AACACAATTT GGCAAATGGA GAGGACAACA AGACGGGGA GAATCACAAT

1801 AATAGTTGGA ATTGTGGTGA GGAAGGAGAA TTTGCAAGTA TCTTTGTGAA

1851 GAAATTGAGG AAAAGACAAA TGCGGAACTT CTTCcTCTGC cTTAtGGTTT

1901 CCCAAGGTGT TCCCATGATA TATATGGGCG ATGAATATGG TCACACTAAG

1951 GGAGGAAACa ACAACACGtA TTGCCATGAT AATTATATTA ATTACTTCCG

2001 TTGGGATAAG AAGGATGAAT CTTCATCTGA TTTTTTGAGA TTTTGCGGCC

2051 TCATGACCAA ATTCCGCCAT GAATGTGAAT CACTGGGATT AGATGGTTTC

2101 CCTACAGCAG AAAGGCTGCA ATGGCATGGT CACACTCCTA GAACTCCAGA

2151 TTGGTCTGAA ACAAGTCGAT TCGTTGCATT CACACTGGTC GACAAAGTGA

2201 AGGGAGAACT ATATATTGCC TTTAACGCCA GCCATTTGCC TGTAACGATT

2251 ACACTTCCAg ATAGGCCTGG TTATAGATGG CAGCCGTTTG TGGACACAGG

2301 CAAACCAGCA CCATTTGACT TCTTGACAGA CGACGTTCCT GAGAGAGAGA

2351 CAGCAGCCAA ACAATATTCT CATTTTCTGG ACGCGAACCA GTATCCGATG

2401 CTCAGTTATT CATCCATTAT TCTTTTACTA TCATCTGCTG ATGATGCATA

2451 GTTTCATTCA CCAAGTTAGG TGGAGGTAAA TCAGCTTCAG ATTTTGTTAT

2501 ATGCAGTGAG GTGTTACTTT GTAAATAAAA GTAAGAAGCA GGACAGAACA

2551 GAACTGCAAA CGGATAAAAT TTGTGAGGAA GAAGCTGATG ATTTATAAGA 2601 tACACCTTGT aTTtTAATtG CATTTATATA AAATAAAATA nTAGTGAAAT

2651 TGTcTGTGcG AAAaaaaaaa AAAAAAAAAA TAAAAAAAAA AAAAAAAAA

2701 AAAAAA

*Fig. 2B*

```
   1  CACAGATTCT CTTCTCCAAA AATAGGGCCC GATGATTAGA GGACCACCAC
  51  AAATCGTCCA GAAATGTCCA ACCGACATTG TAACAGTTAA CCGGACCAAT
 101  ATAGTTCCAC GAACGCACCG TCACGCTCTT CAAGATCTCC GGCAGCTTCG
 151  CCGGCGTGAT AGTCTCAGGC TCTTCTCCTC TGATCACCGG ATTCTGAAGT
 201  TTTGTACATC GGAGGAGGCG TTCCAACCTA GGTTGGTCGC AGCAGCTAAA
 251  CTTCAGGAAG AAGCTCCTCA AATGCTGGAC ACTTTCCCTT CATTCAAAGT
 301  TTCCCCTGGT CTGGCTCATC CACTAGGAGT ATCAGAAACT GAAAGTGGAA
 351  TAAATTTTGC AATTTTTTCT CAGCATGCTT CTGCAGTTAC ACTTTGCATA
 401  ATTCTTCCAA AGAGTGTTCA TGATGGAATG ATTGAATTAG CATTGGATCC
 451  ACAGAAGAAC CGCACAGGAG ACATATGGCA CATATGCATT AAGGAGTTGC
 501  CCCAAGGTGG TGTCCTTTAT GGTTATCGCA TTGATGGACC TCGAAATTGG
 551  CATGAAGGGC ATCGATTTGA TGATAGCATT ATTTTGGTTG ATCCTTACGC
 601  AAAACTAATT GAAGGTCGAC GAGTTTTTGG AGATGAAAGC AATAAAATGT
 651  GTAGATTTTT TGGAACTTAT GATTTCAATA GCTTGCCTTT TGACTGGGGA
 701  GAAAATTACA AGCTTCCAAA TATACCCGAG AAAGATCTTG TTATATATGA
 751  GATGAATGTT CGTGCTTTTA CTGCTGATGA ACAAGTAGT TTGGATCAAG
 801  ATCAACGGGG AAGTTACCTT GGCTTAATTG AAAAGATACC ACATCTTCTC
 851  GAGCTTGGTG TCAATGCAGT AGAATTATTG CCTGTTTTTG AGTTTGATGA
 901  ACTGGAATTA CAAAGGCGAC CTAATCCGAG AGATCACATG ATCAATACAT
 951  GGGGCTACTC AACAATAAAC TTTTTTGCTC CAATGAGTCG ATATGCAAGT
1001  TGTGGTGGCG GACCTGTCCG TGCTTCCTGG GAGTTCAAAG AAATGGTCAA
1051  GGCCTTGCAT GGTGCTGGAA TTGAGGTCAT CTTAGATGTT GTTTATAATC
1101  ACACAAATGA AGCTGATGAT GAAAACCCAT ATACAACCTC ATTCCGAGGA
1151  ATAGACAACA AGGTTTATTA CATGGTAGAT TTAAACAACA ATGCTCAGCT
1201  GCTGAATTTC GCTGGATGTG GAAATACTTT TAACTGCAAC CATCCcACAG
1251  TCATGGAACT TATACTTGAA AGCTTAAGAC ACTGGGTCAC CGAGTATCAT
1301  GTCGATGGAT TCGCTTTGA TCTTGCTAGT GTTCTTTGCA GAGGGACAGA
1351  TGGTACTCCC ATTAATGCTC CCCCCCTTGT TAAGGCCATT TCCAAAGATA
1401  GTGTATTGTC GAGGTGCAAA ATTATTGCTG AGCCATGGGA TTGTGGAGGC
1451  CTATATCTTG TTGGAAAGTT TCCGAACTGG GACCGGTGGG CTGAGTGGAA
1501  TGGGAAGTAC CGCGATGACA TCAGGAGATT TATAAAGGGC GATGCTGGCA
```

*Fig. 3A*

```
1551  TGAAAGGAAA TTTTGCAACC CGTATCGCAG GTTCAGCGGA TCTGTACAGA

1601  GTGAACAAGC GAAAGCCGTA CCACAGTGTC AACTTCGTGA TTGCCCATGA

1651  TGGCTTTACC TTGTATGACC TTGTTTCATA CAATAATAAG CACAATGATG

1701  CAAACGGTGA AGGTGGCAAT GATGGATGCA ATGACAACTT CAGTTGGAAT

1751  TGTGGAATTG AAGGTGAAAC TTCAGATGCA AATATTAACG CACTGCGTTC

1801  ACGGCAAATG AAAAATTTTC ATTTGGCACT GATGGTTTCT CAGGGAACAC

1851  CAATGATGCT TATGGGGGAT GAGTATGGGC ATACCCGCTA TGGAAATAAT

1901  AACAGTTATG GACATGATAC CGCCATCAAC AATTTCCAGT GGGGACAATT

1951  GGAAGCAAGG AAGAATGATC ACTTCAGGTT CTTTCCAAG ATGATAAAGT

2001  TTCGACTGTC CCACAATGTT CTTAGAAAGG AAAACTTCAT TGAGAAGAAC

2051  GACATTACCT GGCTCGAGGA CAACTGGTAC AATGAAGAGA GTAGATTCCT

2101  TGCATTTATG CTCCATGATG GAATGGAGG AGATATTTAC TTGGCATTTA

2151  ATGCACACCA CTTCTCCATC AAAACAGCAA TACCTTCACC ACCACGAAAT

2201  AGAAGTTGGT ACCGAGTGGT GGACACTAAT CTGAAATCAC CAGATGATTT

2251  TGTTACTGAG GGAGTGTCTG GTATCAGTAA AACTTATGAT GTTGCGCCGT

2301  ACTCTGCTAT CCTTCTTGAA GCAAAGCAAT AATTACCGGG ACTATGCTGC

2351  TTTAGATGTT GTCCATGAGT TATTACAGTA TTACCTCCTT CTGGATTGGA

2401  TAGTTCAAAT CGGAATTCAG GCTGTTAGCC TATAGATGTT TGCAATAAGC

2451  AACCAGTTTG TTCAAGCTGC TATTGACAGG TACAAACACC CCATAGTAAT

2501  AAGATAAACT GAGACCATTG ATCCAAAAAA AAAAAAAAAA AAAAAAAAA

2551  AAAAAAAAAA AAAAAAAAAA AAAAAAAAAA AAAAAAAAAA AAAAAAAAA

2601  AAAAAAAAAA AAAAAAAAAA AAAAAAAAAA AAAA
```

*Fig.3B*

```
  1  MATSPIQLAV  HSRLLSYGST  ESTKLVPSSS  GNRGKIVCSL  RKLELEDMNF
 51  SGIGRNNDQE  APRRAHRRKA  LSASRISLVP  SAKRVPTYLF  RTDIGGQVKV
101  LVERTNGKYK  VLVEVLPLEL  SYAHSELVMV  WGLFRSDASC  FMPLDLNRRG
151  ADGKSSTVET  PFVQGPSGKV  TVELDFEASL  APFYISFYMK  SQLVSDMENS
201  EIRSHRNTNF  VVPVGLSSGH  PAPLGISFQP  DGSVNFALFS  RSARSVVLCL
251  YDDISVEKPS  LEIDLDPYIN  RSGDIWHAAL  DCSLPFKTYG  YRCKATTSGK
301  GELVLLDPYA  KVIRRVIPRQ  GGSEIRPKYL  GELCLEPGYD  WSGDVPPSLP
351  MEKLIIYRLN  VTQFTKDKSS  KLPDDLAGTF  SGISEKWHHF  KDLGVNAMLL
401  EPIFPFDEQK  GPYFPWHFFS  PGNMYGPSGD  PLSAIKSMKD  MVKKLHANGI
451  EVFLEVVFTH  TAEDAPLMNV  DNFSYCIKGG  QYLNIQNALN  CNYPIVQQMI
501  LDCLRHWVIE  FHIDGFVFVN  ASSLLRGFNG  EILSRPPLVE  AIAFDPILSK
551  VKMIADNWNP  LTNDSKENLF  PHWRRWAEIN  MRFCDDIRDF  LRGEGLLSNL
601  ATRLCGSGDI  FAGGRGPAFS  FNYIARNSGL  TLVDLVSFSS  NEVASELSWN
651  CGQEGATTNN  IVLERRLKQV  RNFLFILFIS  LGVPVLNMGD  ECGQSSGGPP
701  AYDARKSLGW  NTLKTGFGTQ  IAQFISFLSN  LRMRRSDLLQ  KRTFLKEENI
751  QWHGSDQSPP  KWDGPSSKFL  AMTLKADAEV  SQTLVSDIVG  DLFVAFNGAG
801  DSEIVILPPP  PTDMVWHRLV  DTALPFPGFF  DEKGTPVEDE  LVAYEMKSHS
851  CLLFEAQRLA  EIDSSKRKKQ  IRLSSKRQ
```

*Fig. 4*

```
  1  MELLHCPSIS TYKPKLSFHN HLFSRRSSNG VDFESIWRKS RSSVVNAAVD
 51  SGRGGVVKTA ATAVVVEKPT TERCRFEVLS GKPLPFGATA TDGGVNFAVF
101  SRNATAATLC LITLSDLPEK RVTEQIFLDP LANKTGDVWH VFLKGDFENM
151  LYGYKFDGKF CPEEGHYFDS SQIVLDPYAK AIVSRGEYGV LGPEDDCWPP
201  MAGMVPSASD QFDWEGDLPL KFPQRDLVIY EMHVRGFTNH ESSETKYPGT
251  YLGVVEKLDH LKELGVNCIE LMPCHEFNEL EYYSYNSVLG DYKFNFWGYS
301  TVNFFSPMGR YSSAGLSNCG LGAINEFKYL VKEAHKRGIE VIMDVVFNHT
351  AEGNENGPIL SFRGIDNSVF YTLAPKGEFY NYSGCGNTFN CNNPIVRQFI
401  VDCLRYWVTE MHVDGFRFDL ASILTRSSSS WNAVNVYGNS IDGDVITTGT
451  PLTSPPLIDM ISNDPILRGV KLIAEAWDCG GLYQVGMFPH WGIWSEWNGK
501  YRDMVRQFIK GTDGFSGAFA ECLCGSPNLY QKGGRKPWNS INFVCAHDGF
551  TLADLVTYNN KHNLANGEDN KDGENHNNSW NCGEEGEFAS IFVKKLRKRQ
601  MRNFFLCLMV SQGVPMIYMG DEYGHTKGGN NNTYCHDNYI NYFRWDKKDE
651  SSSDFLRFCG LMTKFRHECE SLGLDGFPTA ERLQWHGHTP RTPDWSETSR
701  FVAFTLVDKV KGELYIAFNA SHLPVTITLP DRPGYRWQPF VDTGKPAPFD
751  FLTDDVPERE TAAKQYSHFL DANQYPMLSY SSIILLLSSA DDA
```

*Fig. 5*

```
  1  MIRGPPQIVQ  KCPTDIVTVN  RTNIVPRTHR  HALQDLRQLR  RRDSLRLFSS
 51  DHRILKFCTS  EEAFQPRLVA  AAKLQEEAPQ  MLDTFPSFKV  SPGLAHPLGV
101  SETESGINFA  IFSQHASAVT  LCIILPKSVH  DGMIELALDP  QKNRTGDIWH
151  ICIKELPQGG  VLYGYRIDGP  RNWHEGHRFD  DSIILVDPYA  KLIEGRRVFG
201  DESNKMCRFF  GTYDFNSLPF  DWGENYKLPN  IPEKDLVIYE  MNVRAFTADE
251  TSSLDQDQRG  SYLGLIEKIP  HLLELGVNAV  ELLPVFEFDE  LELQRRPNPR
301  DHMINTWGYS  TINFFAPMSR  YASCGGGPVR  ASWEFKEMVK  ALHGAGIEVI
351  LDVVYNHTNE  ADDENPYTTS  FRGIDNKVYY  MVDLNNNAQL  LNFAGCGNTF
401  NCNHPTVMEL  ILESLRHWVT  EYHVDGFRFD  LASVLCRGTD  GTPINAPPLV
451  KAISKDSVLS  RCKIIAEPWD  CGGLYLVGKF  PNWDRWAEWN  GKYRDDIRRF
501  IKGDAGMKGN  FATRIAGSAD  LYRVNKRKPY  HSVNFVIAHD  GFTLYDLVSY
551  NNKHNDANGE  GGNDGCNDNF  SWNCGIEGET  SDANINALRS  RQMKNFHLAL
601  MVSQGTPMML  MGDEYGHTRY  GNNNSYGHDT  AINNFQWGQL  EARKNDHFRF
651  FSKMIKFRLS  HNVLRKENFI  EKNDITWLED  NWYNEESRFL  AFMLHDGNGG
701  DIYLAFNAHH  FSIKTAIPSP  PRNRSWYRVV  DTNLKSPDDF  VTEGVSGISK
751  TYDVAPYSAI  LLEAKQ
```

*Fig. 6*

```
  1  AGTAGTTTTT ACACATACTG CTGATTCTGG AGCTCTTCGT GGAATTGATG
 51  ACAGTTCCTA TTACTACAAG GGAAGAGCCA ATNATCTAGA TTCTAAAAGT
101  TACTTGAACT GTAACTATCC TGTTGTTCAG CAGTTGGTAT TGGAGAGCTT
151  GCGTTATTGG GTAACCGAGT TTCATGTAGA TGGATTTTNT TTTATAAATN
201  CTTCATCTCT CTTGAGAGGC GTTCACGGTG AACAGCTCTC TCGTCCTCCT
251  TTGGTTGAAG CAATAGCTTT TNATCCACTT CTTGCGGAGA CCAAACTAAT
301  AGCTGATTGC TGGGNTCCAC TTGAAATGNT GCCANAAGAA GTACGGGTTC
351  CCACAATTTG GAAGCNATNG GCAGAACTCA NNNCAAGGTN TTTTTCGAAA
401  TNTNAGGAAA TTTTTTAAGG GGAANGGG
```

*Fig. 7*

```
  1  MATSPIQLAV HSRLLSYGST ESTKLVPSSS GNRGKIVC
```

*Fig. 8A*

```
  1  MELLHCPSIS TYKPKLSFHN HLFSRRSSNG VDFESIWRKS RSSVVNA
```

```
   1  CTTATGGGAC TTGATTAAGA ATATGTGATC CACCAAGTTC TATATCTGAC
  51  GCTGTTGTAA CATTGTGTGC TGCTAATGGC AACTTCACCA ATACAGTTGG
 101  CTGTGCATTC ACGTTTGTTG AGCTATGGCA GTACTGAGTC AACCAAGTTG
 151  GTTCCTTCAT CATCAGGTAA CCGTGGAAAA ATAGTATGCA GTCTAAGGAA
 201  GCTGGAATTG GAAGACATGA ATTTCTCTGG CATAGGTCGA AATAATGATC
 251  AAGAAGCTCC TAGGAGAGCT CATCGACGAA AAGCACTATC AGCATCGAGA
 301  ATTTCGCTTG TTCCATCTGC AAAAAGGGTT CCCACTTACC TTTTCAGGAC
 351  AGATATTGGT GGTCAAGTGA AAGTCTTGGT GGAAAAGACA AATGGAAAGT
 401  ACAAAGTGCT TGTAGAAgTC TTGCCATTGG AGCTCTCAGA TGCACATTCT
 451  GAGCTAGTTA TGGTTTGGGG TCTTTTTAGA TCTGATGCTT TATGCTTTAT
 501  GCCTCTGGAT CTAAACAGAC GTGGAGCAGA TGGAAAAAGT AGTACTGTTG
 551  AAACACCATT TGTGCAAGGA CCTTCAGGCA AGGTCACCGT GGAGCTGGAT
 601  TTTGAAGCAA GTTTAGCCCC CTTCTATATC TCCTTCTATA TGAAGTCACA
 651  ACTAGTTTCT GACATGGAAA ACTCAGAAAT CAGAAGTCAC AGGAACACAA
 701  ATTTTGTTGT ACCAGTTGGT CTCAGTTCAG GCATCCTGC TCCATTGGGT
 751  ATTTCCTTTC AGCCAGATGG ATCTGTGAAT TTTGCTCTCT TCTCACGCAG
 801  TGCAAGAAGT GTAGTTCTGT GCTTGTATGA TGACATATCA GTTGAAAAAC
 851  CTTCTTTAGA GATTGATCTA GATCCTTATA TTAATCGATC AGGCGATATT
 901  TGGCATGCTG CTTTAGATTG TTCTTTGCCA TTTAAGACTT ATGGTTATAG
 951  ATGTAAGGCG ACTACTTCTG GGAAGGGAGA GCTGGTTCTT TTGGACCCAT
1001  ATGCTAAGGT GATAAGGCGT GTTATTCcTc GTCAGGGTGG GTCTGAGATA
1051  CGTCCAAAAT ATCTTGGAGA ACTATGCCTG GAACCTGGCT ATGATTGGAG
1101  CGGTGATGTC CCCCCTAGCT TACCTATGGA GAAACTAATA ATTTACCGCT
1151  TAAATGTGAC TCAATTTACA AAGGACAAGT CCAGTAAGCT ACCTGATGAC
1201  CTTGCTGGAA CTTTcTcTGG CATTAGCGAA AAATGGCACC ATTTTAAAGA
1251  TCTTGGTGTG AATGCAATGT TACTGGAGCC AATTTTCCcT TTTGATGAGC
1301  AGAAAGGACC CTATTTTCCG TGGCATTTCT TTTCACCTGG AAATATGTAT
1351  GGACCTTCTG GTGACCCTCT TTCTGCCATT AAATCGATGA AGGATATGGT
1401  TAAGAAATTA CATGCTAACG GGATAGAGGT TTTTCTTGAA GTTGTTTTCA
1451  CTCACACTGC AGAGGATGCA CCTTTGATGA ATGTTGATAA CTTTTCATAT
1501  TGCATAAAAG GTGGTCAGTA TCTGAATATT CAAAATGCAT TGAATTGCAA
```

```
1551   TTACCCCATA GTCCAACAAA TGATTTTGGA CTGTCTCCGC CACTGGGTAA

1601   TTGAGTTTCA TATTGATGGT TTTGTTTTTG TCAACGCTTC TTCCTTGTTG

1651   AGAGGGTTCA ATGGAGAGAT TCTATCTCGT CCTCCATTAg TTgaagcTaT

1701   TGCCTTTGAT CCTATCCTTT CAAAGGTCAA GATGATTGCA GATAATTGGA

1751   ATCCATTAAC CAATGATTCG AAGGAAAATT TATTCCCTCA CTGGAGGAGA

1801   TGGGCAGAGA TAAATATGAG ATTTTGTGAT GACATTCGAG ACTTCTTGAG

1851   AGGCGAgGGT CTTCTAAnCA ATCTAnCAAC ACgACTTTGT GGAAGTGGGG

1901   ATATCTTCGC AGGTGGACGT GGTCCTGCAT TCTCTTTTAA TTATATTGCC

1951   AGAAATTCTG GACTCACACT TGTTGACCTA GTTAGCTTCA GTAGTAATGA

2001   AGTGGCTTCA GAGTTAAGTT GGAACTGTGG ACAAGAAGGC GCTACGACCA

2051   ATAACATTGT CCTAGAGAGA CGACTTAAAC AAGTTCGTAA TTTTCTGTTC

2101   ATATTGTTCA TTTCTCTAGG TGTACCAGTA CTTAACATGG GAGACGAGTG

2151   TGGTCAGTCT TCAGGAGGTC CCCCTGCaTa TgATgCTCGA AAATCTTTGG

2201   GTTGGAATAC TTTAAAAACT GGTTTTGGGA CTCAGATTGC CCAGTTTATT

2251   TCATTCTTGA GTAATTTAAG AATGAGAAGA AGTGATCTTC TTCAAAAGAG

2301   AACCTTCTTG AAGGAAGAAA ACATCCAGTG GCATGGGAGT GACCAATCTC

2351   CTCCGAAATG GGATGGCCCG TCTAGCAAAT TCTTGGCTAT GACTTTGAAG

2401   GCCGATGCTG AAGTCAGCCA GACATTAGTC TCTGATATCG TAGGTGACCT

2451   GTTTGTTGCT TTCAATGGTG CTGGTGATTC AGAGATTGTT ATCCTTCCAC

2501   CTCCTCCAAC AGATATGGTA TGGCATCGTC TCGTTGACAC AGCCCTCCCT

2551   TTCCCGGGGT TTTTCGATGA GAAGGGAACT CCAGTTGAAG ATGAATTAGT

2601   TGCTTATGAG ATGAAGTCTC ACAGCTGTTT GCTGTTTGAA GCTCAGAGAC

2651   TAGCTGAAAT AGATTCTAGC AAGAGAAAGA AACAGATTAG ACTTTcTTcT

2701   AAGAGGCAAT AGTTTGTAAA GCCCTAAGT ATATATATAT GTTTAAATAA

2751   GAGGCTTTTT TTTCTGAATA AATAAGAAGA TTTTACTGAG AATACTTGTA

2801   TCTAAACATT TTCTTTTGCA GCTTCAAATA AAAAAAAAAA AAA
```

```
   1 GGCGGCCGCT CTAGAACTAG TGGATCCCCC GGGCTGCAGG AATTCGAGGA
  51 TCCGGGTACC ATGGCTCAGT CCTTCTCAAT TTCAGTGCCA CATACTCTAG
 101 ATCACACTCT CTCTCTTCCT CAAAGTTCTC CCATGGAGTT ACTTCATTGT
 151 CCTTCCATTT CTACCTACAA ACCTAAACTC TCTTTCCACA ACCATCTTTT
 201 CTCGAGGAGA AGCAGTAACG GTGTAgATTT TGAGAGTATT TGGAGAAAAT
 251 CGAGGTCTTC AGTGGTTAAT GCTGCTGTTG ATAGTGGACG TGGAGGTGTG
 301 GTGAAGACTG CGGCTACTGC GGTGGTGGTG GAGAAGCCGA CGACGGAACG
 351 ATGTCGTTTG AGGTTTTATC AGGGAAAGCC ATTGCCGTTT GGTGCTACTG
 401 CGACAGATGG TGGTGTGAAT TCGCTGTTT TTCAAGGAAA TGCTACAGCT
 451 GCTACTCTTT GCTTGATCAC TCTTTCCGAT TTACCTGAGA AGAGAGTGAC
 501 CGAGCAAATT TTCCTGGATC CTCTAGCTAA TAAAACTGGA GATGTATGGC
 551 ATGTGTTCCT TAAGGGAGAT TTTGAGAATA TGCTATATGG CTACAAATTT
 601 GATGGGAAAT TCTGTCCTGA AGAAGGACAC TACTTTGACT CTTCGCAGAT
 651 AGTGTTGGAT CCTTATGCCa agGCTATAGT AAGCAGAGGA GAATATGGTG
 701 TATTAGGGCC AGAGGATGAT TGTTGGCCCC CAATGGCTGG CATGGTACCc
 751 TTCTGCTTCT GgATCAGTTT GTATTGGGAA GGAGATCTAC CACTGgAAGT
 801 TTCCcACAgA GAGATCTTGT TnATCnATGA AATGCATGTT CGTGGGTTTA
 851 CTATCCATGA GTCGAGTGAA ACAAAATATC CTGGTACTTA CCTTGGTGTT
 901 GTGGAGAAAC TTGATCACTT GAAGGAACTT GGTGTCAACT GTATAGAGCT
 951 AATGCCCTGT CACGAGTTCA ATGAGCTGGA GTACTATAGT TATAACTCTG
1001 TATTGGGCGA CTACAAGTTT AACTTTTGGG GCTATTCTAC TGTCAATTTC
1051 TTTTCTCCAA TGGGAAGATA CTCATCTGCT GGTCTAAGTA ATTGCGGCCT
1101 CGGTGCAATA AACgAATTTA AGTATCTTGT CAAGGAAGCA CATAAACGTG
1151 GAATCGAgGT TATCATGGAT GTTGTTTTCA ATCACACTGC TGAAGGAAAT
1201 GAAAATGGTC CCATACTATC ATTTAgAgGC ATTGACAACA GTGTGTTTTA
1251 TACGCTAGCT CCTAAGGGTg AATTTTACAA CTACTCAgGA TGTGGAAATA
1301 CCtTCAACTG TAATAATCCC ATTGTACGTC AATtTATAgT GATGCTGAgA
1351 TATtGGGTTA CCGAAATGCA CGTaCATGGC TTCCGCTTTG ATCTTGCTTC
1401 TATCCTTACA AGAAGTAGCA GCTCGTGGAA TGCTGTAAAT GTCTATGGAA
1451 ATTCAATTGA CGGTGACGTG ATCaCCACAG GCACTCCTCT CACAAGCCCA
1501 CCATTGATTG ATATGATTAG CAATGATCCA ATACTTCGTG GAGTAAAGCT
```

```
1551  TATAGCTGAA GCATGGGATT GTGGAGGCCT TTACCAAGTT GGCATGTTTC
1601  CGCACTGGGG TATCTGGTCG GAGTGGAACG GAAAGTACCG TGACATGGTA
1651  CGGCAGTTCA TCAAAGGCAC TGATGGGTTT TCTGGGGCTT TTGCTGAATG
1701  CCTTTGTGGA AGCCCAAATC TATACCAGAA AGGAGGAAGA AAACCATGGA
1751  ACAGTATAAA TTTCGTGTGT GCCCACGATG GTTTTACTTT GGCTGATTTA
1801  GTGACATACA ACAATAAACA CAATTTGGCA AATGGAGAGG ACAACAAAGA
1851  CGGGGAGAAT CACAATAATA GTTGGAATTG TGGTGAGGAA GGAGAATTTG
1901  CAAGTATCTT TGTGAAGAAA TTGAGGAAAA GACAAATGCG GAACTTCTTC
1951  cTCTGCcTTA tGGTTTCCCA AGGTGTTCCC ATGATATATA TGGGCGATGA
2001  ATATGGTCAC ACTAAGGGAG GAAACaACAA CACGtATTGC CATGATAATT
2051  ATATTAATTA CTTCCGTTGG GATAAGAAGG ATGAATCTTC ATCTGATTTT
2101  TTGAGATTTT GCGGCCTCAT GACCAAATTC CGCCATGAAT GTGAATCACT
2151  GGGATTAGAT GGTTTCCCTA CAGCAGAAAG GCTGCAATGG CATGGTCACA
2201  CTCCTAGAAC TCCAGATTGG TCTGAAACAA GTCGATTCGT TGCATTCACA
2251  CTGGTCGACA AAGTGAAGGG AGAACTATAT ATTGCCTTTA ACGCCAGCCA
2301  TTTGCCTGTA ACGATTACAC TTCCAgATAG GCCTGGTTAT AGATGGCAGC
2351  CGTTTGTGGA CACAGGCAAA CCAGCACCAT TGACTTCTT GACAGACGAC
2401  GTTCCTGAGA GAGAGACAGC AGCCAAACAA TATTCTCATT TTCTGGACGC
2451  GAACCAGTAT CCGATGCTCA GTTATTCATC CATTATTCTT TTACTATCAT
2501  CTGCTGATGA TGCATAGTTT CATTCACCAA GTTAGGTGGA GGTAAATCAG
2551  CTTCAGATTT TGTTATATGC AGTGAGGTGT TACTTTGTAA ATAAAAGTAA
2601  GAAGCAGGAC AGAACAGAAC TGCAAACGGA TAAAATTTGT GAGGAAGAAG
2651  CTGATGATTT ATAAGAtACA CCTTGTaTTt TAATtGCATT TATATAAAAT
2701  AAAATAnTAG TGAAATTGTc TGTGcGAAAa aaaaaaAAAA AAAAAATAAA
2751  AAAAAAAAAA AAAAAAAAAA AACCATGGTA CCCGGATCCT CGAATTnGAT
2801  ATCAAG
```

```
   1  CTCATTCCGA GGAATAGACA ACAAGGTTTA TTACATGGTA GATTTGAACA
  51  ACAATGCTCA GCTGCTGAAT TTCGCTGGAT GTGGAAATAC TTTTAACTGC
 101  AATCATCCTA CAGTCATGGA ACTTATACTT GAAAGCTTAA GACACTGGGT
 151  CACCGAGTAT CATGTCGATG GATTTCGCTT TGATCTTGCT AGTGTTCTTT
 201  GCAGAGGGAC AGATGGTACT CCCATTAATG CTCCCCCCCT TGTAAAGGCC
 251  ATTTCCAAAG ATAGTGTATT GTCGAGGTGC AAAATTATTG CTGAGCCATG
 301  GGATTGTGGA GGCCTATATC TTGTTGGAAA GTTTCCGAAC TGGGACCGGT
 351  GGGCTGAGTG GAATGGGAAG TACCGCGATG ACATCAGGAG ATTTATAAAG
 401  GGCGATGCTG GCATGAAAGG AAATTTTGCA ACCCGTATCG CAGGTTCAGC
 451  GGATCTGTAC AGAGTGAACA AGCGAAAGCC GTACCACAGT GTCAACTTCG
 501  TGATTGCCCA TGATGGCTTT ACCTTGTATG ACCTTGTTTC ATACAATAAT
 551  AAGCACAATG ATGCGAACGG TGAAGGTGGC AATGATGGAT GCAATGACAA
 601  CTTCAGTTGG AATTGTGGAA TTGAAGGTGA ACTTCAGAT GCAAATATTA
 651  ACGCACTGCG TTCACGGCAA ATGAAAAATT TTCATTTGGC ACTGATGGTT
 701  TCTCAGGGAA CACCAATGAT GCTTATGGGG GATGAGTATG GGCATACCCG
 751  CTATGGAAAT AATAACAGTT ATGGACATGA TACCGCCATC AACAATTTCC
 801  AGTGGGGACA ATTGGAAGCA AGGAAGAATG ATCACTTCAG GTTCTTTTCC
 851  AAGATGATAA AGTTTCGACT GTCCCACaAt GTTCTTAGAA AGGAaAACTT
 901  CATTGAGAAG AACGACATTA CCTGGCTCGA GGACAACTGG TACAATGAAG
 951  AGAGTAGATT CCTTGCATTT ATGCTCCATG ATGGGAATGG AGGAGATATT
1001  TACTTGGCAT TTAATGCACA CCACTTTTCC ATCAAAACAG CAATACCTTC
1051  ACCACCACGA AATAGAAGTT GGTACCGAGT GGTGGACACT AATCTGAAGT
1101  CACCAGATGA TTTTGTTATT GAGGGAGTGT CTGGTATCAG TGAAACTTAT
1151  GATGTTGCGC CGTACTCTGC TATCCTTCTT GAAGCAAAGC AATAATTACC
1201  GGGACTATGC TGCTTTAGAT GTTGTCCATG TGTTATTACA GTATTACCTC
1251  CTTCTGGATT GGATAGTTCA AATTGGAATT CAGGCTGTTA GCCTATAGAT
1301  GTAGTATGTT GAGCAGAAAT TTTGCAATAA GCAACCAGTT TTGTTCAAAA
1351  AAAAAAAAAA AAAAAAAAAA AAAAAAAAAA AAAAAAAAA
```

```
  1  LMGLD*EYVI  HQVLYLTLL*  HCVLLMATSP  IQLAVHSRLL  SYGSTESTKL
 51  VPSSSGNRGK  IVCSLRKLEL  EDMNFSGIGR  NNDQEAPRRA  HRRKALSASR
101  ISLVPSAKRV  PTYLFRTDIG  GQVKVLVEKT  NGKYKVLVEV  LPLELSDAHS
151  ELVMVWGLFR  SDALCFMPLD  LNRRGADGKS  STVETPFVQG  PSGKVTVELD
201  FEASLAPFYI  SFYMKSQLVS  DMENSEIRSH  RNTNFVVPVG  LSSGHPAPLG
251  ISFQPDGSVN  FALFSRSARS  VVLCLYDDIS  VEKPSLEIDL  DPYINRSGDI
301  WHAALDCSLP  FKTYGYRCKA  TTSGKGELVL  LDPYAKVIRR  VIPRQGGSEI
351  RPKYLGELCL  EPGYDWSGDV  PPSLPMEKLI  IYRLNVTQFT  KDKSSKLPDD
401  LAGTFSGISE  KWHHFKDLGV  NAMLLEPIFP  FDEQKGPYFP  WHFFSPGNMY
451  GPSGDPLSAI  KSMKDMVKKL  HANGIEVFLE  VVFTHTAEDA  PLMNVDNFSY
501  CIKGGQYLNI  QNALNCNYPI  VQQMILDCLR  HWVIEFHIDG  FVFVNASSLL
551  RGFNGEILSR  PPLVEAIAFD  PILSKVKMIA  DNWNPLTNDS  KENLFPHWRR
601  WAEINMRFCD  DIRDFLRGEG  LLxNLxTRLC  GSGDIFAGGR  GPAFSFNYIA
651  RNSGLTLVDL  VSFSSNEVAS  ELSWNCGQEG  ATTNNIVLER  RLKQVRNFLF
701  ILFISLGVPV  LNMGDECGQS  SGGPPAYDAR  KSLGWNTLKT  GFGTQIAQFI
751  SFLSNLRMRR  SDLLQKRTFL  KEENIQWHGS  DQSPPKWDGP  SSKFLAMTLK
801  ADAEVSQTLV  SDIVGDLFVA  FNGAGDSEIV  ILPPPPTDMV  WHRLVDTALP
851  FPGFFDEKGT  PVEDELVAYE  MKSHSCLLFE  AQRLAEIDSS  KRKKQIRLSS
901  KRQ*FVKPLS  IYICLNKRLF  FLNK*EDFTE  NTCI*TFSFA  ASNKKKK
```

*Fig. 13*

```
  1  GGRSRTSGSP  GLQEFEDPGT  MAQSFSISVP  HTLDHTLSLP  QSSPMELLHC
 51  PSISTYKPKL  SFHNHLFSRR  SSNGVDFESI  WRKSRSSVVN  AAVDSGRGGV
101  VKTAATAVVV  EKPTTERCRL  RFYQGKPLPF  GATATDGGVN  FAVFQGNATA
151  ATLCLITLSD  LPEKRVTEQI  FLDPLANKTG  DVWHVFLKGD  FENMLYGYKF
201  DGKFCPEEGH  YFDSSQIVLD  PYAKAIVSRG  EYGVLGPEDD  CWPPMAGMVP
251  FCFWISLYWE  GDLPLEVSHR  EILxIxEMHV  RGFTIHESSE  TKYPGTYLGV
301  VEKLDHLKEL  GVNCIELMPC  HEFNELEYYS  YNSVLGDYKF  NFWGYSTVNF
351  FSPMGRYSSA  GLSNCGLGAI  NEFKYLVKEA  HKRGIEVIMD  VVFNHTAEGN
401  ENGPILSFRG  IDNSVFYTLA  PKGEFYNYSG  CGNTFNCNNP  IVRQFIVMLR
451  YWVTEMHVHG  FRFDLASILT  RSSSSWNAVN  VYGNSIDGDV  ITTGTPLTSP
501  PLIDMISNDP  ILRGVKLIAE  AWDCGGLYQV  GMFPHWGIWS  EWNGKYRDMV
551  RQFIKGTDGF  SGAFAECLCG  SPNLYQKGGR  KPWNSINFVC  AHDGFTLADL
601  VTYNNKHNLA  NGEDNKDGEN  HNNSWNCGEE  GEFASIFVKK  LRKRQMRNFF
651  LCLMVSQGVP  MIYMGDEYGH  TKGGNNNTYC  HDNYINYFRW  DKKDESSSDF
701  LRFCGLMTKF  RHECESLGLD  GFPTAERLQW  HGHTPRTPDW  SETSRFVAFT
751  LVDKVKGELY  IAFNASHLPV  TITLPDRPGY  RWQPFVDTGK  PAPFDFLTDD
801  VPERETAAKQ  YSHFLDANQY  PMLSYSSIIL  LLSSADDA*F  HSPS*VEVNQ
851  LQILLYAVRC  YFVNKSKKQD  RTELQTDKIC  EEEADDL*DT  PCILIAFI*N
901  KIxVKLSVRK  KKKKKIKKKK  KKKKPWYPDP  RIxYQ
```

*Fig. 14*

```
  1  SFRGIDNKVY  YMVDLNNNAQ  LLNFAGCGNT  FNCNHPTVME  LILESLRHWV
 51  TEYHVDGFRF  DLASVLCRGT  DGTPINAPPL  VKAISKDSVL  SRCKIIAEPW
101  DCGGLYLVGK  FPNWDRWAEW  NGKYRDDIRR  FIKGDAGMKG  NFATRIAGSA
151  DLYRVNKRKP  YHSVNFVIAH  DGFTLYDLVS  YNNKHNDANG  EGGNDGCNDN
201  FSWNCGIEGE  TSDANINALR  SRQMKNFHLA  LMVSQGTPMM  LMGDEYGHTR
251  YGNNNSYGHD  TAINNFQWGQ  LEARKNDHFR  FFSKMIKFRL  SHNVLRKENF
301  IEKNDITWLE  DNWYNEESRF  LAFMLHDGNG  GDIYLAFNAH  HFSIKTAIPS
351  PPRNRSWYRV  VDTNLKSPDD  FVIEGVSGIS  ETYDVAPYSA  ILLEAKQ*LP
401  GLCCFRCCPC  VITVLPPSGL  DSSNWNSGC*  PIDVVC*AEI  LQ*ATSFVQK
451  KKKKKKKKK   KK
```

*Fig. 15*

```
  1  GATCATAACT  TGAGTTCTAA  GCGG
```

*Fig. 16A*

```
  1  CAGGAAACAG  CTATGAC
```

*Fig. 16B*

SEQUENCE LISTING

```
<160> NUMBER OF SEQ ID NOS: 30

<210> SEQ ID NO 1
<211> LENGTH: 2843
<212> TYPE: DNA
<213> ORGANISM: Solanum tuberosum

<400> SEQUENCE: 1
cttatgggac ttgattaaga atatgtgatc caccaagttc tatatctgac gctgtcgtaa      60
cattgtgtgc tgctaatggc aacttcacca atacagttgg ctgtgcattc acgtttgttg     120
agctatggca gtactgagtc aaccaagttg gttccttcat catcaggtaa ccgtggaaaa     180
atagtatgca gtctaaggaa gctggaattg gaagacatga atttctctgg cataggtcga     240
aataatgatc aagaagctcc taggagagct catcgacgaa aagcactatc agcatcgaga     300
atttcgcttg ttccatctgc aaaaagggtt cccacttacc ttttcaggac agatattggt     360
ggtcaagtga aagtcttggt ggaaaggaca aatggaaagt acaaagtgct tgtagaagta     420
ttgccattgg agctctcata tgcacattct gagctggtta tggtttgggg tcttttttaga    480 tctgatgctt catgctttat gcctctagat ctaaatagac gtggagcaga tggaaaaagt     540
agtactgttg aaacaccatt tgtgcaagga ccttcaggca aggtcaccgt ggagctggat     600
tttgaagcaa gtttagcccc cttctatatc tccttctata tgaagtcgca actagtttct     660
gacatggaaa actcagaaat cagaagtcac aggaacacaa attttgttgt accagttggt     720
ctcagttcag ggcatcctgc tccattgggt atttcctttc agccagatgg atctgtgaat     780
tttgctctct tctcacgcag tgcaagaagt gtagttctgt gcttgtatga tgacatatca     840
gttgaaaaac cttctttaga gattgatcta gatccttata ttaatcgatc aggcgatatt     900
```

```
tggcatgctg ctttagattg ttctttgcca tttaagactt atggttatag atgtaaggcg    960
actacttctg ggaagggaga gctggttctt ttggacccat atgctaaggt gataaggcgt   1020
gttattcctc gtcagggtgg gtctgagata cgtccaaaat atcttggaga actatgcctg   1080
gaacctggct atgattggag cggtgatgtc cccctagct tacctatgga gaaactaata   1140
atttaccgct taaatgtgac tcaatttaca aaggacaagt ccagtaagct acctgatgac   1200
cttgctggaa ctttctctgg cattagcgaa aaatggcacc attttaaaga tcttggtgtg   1260
aatgcaatgt tactggagcc aatttccct tttgatgagc agaaaggacc ctattttccg   1320
tggcatttct tctcacctgg aaatatgtat ggaccttctg gtgaccctct ttctgccatt   1380
aaatcgatga aggatatggt taagaaatta catgctaacg ggatagaggt ttttcttgaa   1440
gttgttttca ctcacactgc agaggatgca cctttgatga atgttgataa cttttcatat   1500
tgcataaaag gtggtcagta tctgaatatt caaaatgcat tgaattgcaa ttaccccata   1560
gtccaacaaa tgattttgga ctgtctccgc cactgggtaa ttgagtttca tattgatggt   1620
tttgtttttg tcaacgcttc ttccttgttg agagggttca atggagagat tctatctcgt   1680
cctccattag ttgaagctat tgcctttgat cctatccttt caaggtcaa gatgattgca   1740
gataattgga atccattaac caatgattcg aaggaaaatt tattccctca ctggaggaga   1800
tgggcagaga taaatatgag attttgtgat gacattcgag acttcttgag aggcgagggt   1860
cttctaagca atctagcaac acgactttgt ggaagtgggg atatcttcgc aggtggacgt   1920
ggtcctgcat tctcttttaa ttatattgcc agaaattctg gactcacact tgttgaccta   1980
gttagcttca gtagtaatga agtggcttca gagttaagtt ggaactgtgg acaagaaggc   2040
gctacgacca ataacattgt cctagagaga cgacttaaac aagttcgtaa ttttctgttc   2100
atattgttca tttctctagg tgtaccagta cttaacatgg gagacgagtg tggtcagtct   2160
tcaggaggtc ccctgcata tgatgctcga aaatctttgg gttggaatac tttaaaaact   2220
ggttttggga ctcagattgc ccagtttatt tcattcttga gtaatttaag aatgagaaga   2280
agtgatcttc ttcaaaagag aaccttcttg aaggaagaaa acatccagtg gcatgggagt   2340
gaccaatctc ctccgaaatg ggatggcccg tctagcaaat tcttggctat gactttgaag   2400
gccgatgctg aagtcagcca gacattagtc tctgatatcg taggtgacct gtttgttgct   2460
ttcaatggtg ctggtgattc agagattgtt atccttccac ctcctccaac agatatggta   2520
tggcatcgtc tcgttgacac agccctccct ttcccggggt ttttcgatga aagggaact   2580
ccagttgaag atgaattagt tgcttatgag atgaagtctc acagctgttt gctgtttgaa   2640
gctcagagac tagctgaaat agattctagc aagagaaaga aacagattag actttcttct   2700
aagaggcaat agtttgtaaa gcccctaagt atatatatat gtttaaataa gaggcttttt   2760
tttctgaata aataagaaga ttttactgag aatacttgta tctaaacatt ttcttttgca   2820
gcttcaaata aaaaaaaaa aaa                                            2843
```

<210> SEQ ID NO 2
<211> LENGTH: 2706
<212> TYPE: DNA
<213> ORGANISM: Solanum tuberosum
<220> FEATURE:
<221> NAME/KEY: misc_feature
<222> LOCATION: (2641)
<223> OTHER INFORMATION: n = a or g or c or t

<400> SEQUENCE: 2

-continued

```
ctcagtcctt ctcaatttca gtgccacata ctctagatca cactctctct tcttcctcaa      60
agttctccca tggagttact tcattgtcct tccatttcta cctacaaacc taaactctct     120
ttccacaacc atcttttctc gaggagaagc agtaacggtg tagattttga gagtattttgg    180 agaaaatcga ggtcttcagt ggttaatgct gctgttgata gtggacgtgg aggtgtggtg     240
aagactgcgg ctactgcggt ggtggtggag aagccgacga cggaacgatg tcgttttgag     300
gttttatcag ggaagccatt gccgtttggt gctactgcga cagatggtgg tgtgaatttc     360 gctgttttt caaggaatgc tacagctgct actctttgct tgatcactct ttccgattta      420
cctgagaaga gagtgaccga gcaaattttc ctggatcctc tagctaataa aactggagat     480
gtatggcatg tgttccttaa gggagatttt gagaatatgc tatatggcta caaatttgat     540
gggaaattct gtcctgaaga aggacactac tttgactctt cgcagatagt gttggatcct     600
tatgccaagg ctatagtaag cagaggagaa tatggtgtat tagggccaga ggatgattgt     660 tggccccaa tggctggcat ggtaccttct gcttctgatc agtttgattg ggaaggagat      720
ctaccactga gtttccaca gagagatctt gtaatctatg aaatgcatgt tcgtgggttt      780
actaatcatg agtcgagtga aacaaaatat cctggtactt accttggtgt tgtggagaaa     840
cttgatcact tgaaggaact tggtgtcaac tgtatagagc taatgccctg tcacgagttc     900
aatgagctgg agtactatag ttataactct gtattgggcg actacaagtt taactttgg     960 ggctattcta ctgtcaattt cttttctcca atgggaagat actcatcgc tggtctaagt    1020 aattgcggcc tcggtgcaat aaacgaattt aagtatcttg tcaaggaagc atataaacgt    1080
ggaatcgagg ttatcatgga tgttgtttc aatcacactg ctgaaggaaa tgaaaatggt    1140
cccatactat catttagagg cattgacaac agtgtgtttt tacgctagc tcctaagggg    1200 gaattttaca actactcagg atgtggaaat accttcaact gtaataatcc cattgtacgt    1260
caatttatag tggattgctt gagatattgg gttaccgaaa tgcacgtaga tggcttccgc    1320
tttgatcttg cttctatcct tacaagaagt agcagctcgt ggaatgctgt aaatgtctat    1380
ggaaattcaa ttgacggtga cgtgatcacc acaggcactc ctctcacaag cccaccattg    1440
attgatatga ttagcaatga tccaatactt cgtggagtaa agcttatagc tgaagcatgg    1500
gattgtggag gcctttacca agttggcatg tttccgcact ggggtatctg gtcggagtgg    1560
aacggaaagt accgtgacat ggtacggcag ttcatcaaag gcactgatgg gttttctggg    1620
gcttttgctg aatgcctttg tggaagccca aatctatacc agaaaggagg aagaaaacca    1680
tggaacagta taaatttcgt gtgtgcccac gatggttttta cttttggctga tttagtgaca    1740 tacaacaata aacacaattt ggcaaatgga gaggacaaca aagacgggga gaatcacaat    1800
aatagttgga attgtggtga ggaaggagaa tttgcaagta tctttgtgaa gaaattgagg    1860
aaaagacaaa tgcggaactt cttcctctgc cttatggttt cccaaggtgt tcccatgata    1920
tatatgggcg atgaatatgg tcacactaag ggaggaaaca acaacacgta ttgccatgat    1980
aattatatta attacttccg ttgggataag aaggatgaat cttcatctga ttttttgaga    2040
ttttgcggcc tcatgaccaa attccgccat gaatgtgaat cactgggatt agatggtttc    2100
cctacagcag aaaggctgca atggcatggt cacactccta gaactccaga ttggtctgaa    2160
acaagtcgat tcgttgcatt cacactggtc gacaaagtga agggagaact atatattgcc    2220
tttaacgcca gccatttgcc tgtaacgatt acacttccag ataggcctgg ttatagatgg    2280
cagccgtttg tggacacagg caaaccagca ccatttgact tcttgacaga cgacgttcct    2340
gagagagaga cagcagccaa acaatattct catttttctgg acgcgaacca gtatccgatg    2400
```

-continued

```
ctcagttatt catccattat tcttttacta tcatctgctg atgatgcata gtttcattca    2460
ccaagttagg tggaggtaaa tcagcttcag attttgttat atgcagtgag gtgttacttt    2520
gtaaataaaa gtaagaagca ggacagaaca gaactgcaaa cggataaaat ttgtgaggaa    2580
gaagctgatg atttataaga tacaccttgt attttaattg catttatata aaataaaata    2640
ntagtgaaat tgtctgtgcg aaaaaaaaaa aaaaaaaaaa taaaaaaaaa aaaaaaaaaa    2700
aaaaaa                                                               2706

<210> SEQ ID NO 3
<211> LENGTH: 2634
<212> TYPE: DNA
<213> ORGANISM: Solanum tuberosum

<400> SEQUENCE: 3
cacagattct cttctccaaa aatagggccc gatgattaga ggaccaccac aaatcgtcca      60
gaaatgtcca accgacattg taacagttaa ccggaccaat atagttccac gaacgcaccg     120
tcacgctctt caagatctcc ggcagcttcg ccggcgtgat agtctcaggc tcttctcctc     180
tgatcaccgg attctgaagt tttgtacatc ggaggaggcg ttccaaccta ggttggtcgc     240
agcagctaaa cttcaggaag aagctcctca atgctggac  actttccctt cattcaaagt     300
ttcccctggt ctggctcatc cactaggagt atcagaaact gaaagtggaa taaattttgc     360
aattttttct cagcatgctt ctgcagttac actttgcata attcttccaa agagtgttca     420
tgatggaatg attgaattag cattggatcc acagaagaac cgcacaggag acatatggca     480
catatgcatt aaggagttgc cccaaggtgg tgtcctttat ggttatcgca ttgatggacc     540
tcgaaattgg catgaagggc atcgatttga tgatagcatt attttggttg atccttacgc     600
aaaactaatt gaaggtcgac gagttttttgg agatgaaagc aataaaatgt gtagattttt     660
tggaacttat gatttcaata gcttgccttt tgactgggga gaaaattaca agcttccaaa     720
tatacccgag aaagatcttg ttatatatga gatgaatgtt cgtgctttta ctgctgatga     780
aacaagtagt ttggatcaag atcaacgggg aagttacctt ggcttaattg aaaagatacc     840
acatcttctc gagcttggtg tcaatgcagt agaattattg cctgttttg agtttgatga     900 actggaatta caaaggcgac ctaatccgag agatcacatg atcaatacat ggggctactc     960
aacaataaac ttttttgctc caatgagtcg atatgcaagt tgtggtggcg gacctgtccg    1020
tgcttcctgg gagttcaaag aaatggtcaa ggccttgcat ggtgctggaa ttgaggtcat    1080
cttagatgtt gtttataatc acacaaatga agctgatgat gaaaacccat atacaacctc    1140
attccgagga atagacaaca aggtttatta catggtagat taaacaaca atgctcagct    1200 gctgaatttc gctggatgtg gaaatacttt taactgcaac catcccacag tcatggaact    1260
tatacttgaa agcttaagac actgggtcac cgagtatcat gtcgatggat ttcgctttga    1320
tcttgctagt gttctttgca gagggacaga tggtactccc attaatgctc ccccccttgt    1380
taaggccatt tccaaagata gtgtattgtc gaggtgcaaa attattgctg agccatggga    1440
ttgtggaggc ctatatcttg ttggaaagtt tccgaactgg gaccggtggg ctgagtggaa    1500
tgggaagtac cgcgatgaca tcaggagatt tataaagggc gatgctggca tgaaaggaaa    1560
ttttgcaacc cgtatcgcag gttcagcgga tctgtacaga gtgaacaagc gaaagccgta    1620
ccacagtgtc aacttcgtga ttgcccatga tggcttacc ttgtatgacc ttgtttcata    1680
caataataag cacaatgatg caaacggtga aggtggcaat gatggatgca atgacaactt    1740
```

```
cagttggaat tgtggaattg aaggtgaaac ttcagatgca aatattaacg cactgcgttc    1800
acggcaaatg aaaaattttc atttggcact gatggtttct cagggaacac caatgatgct    1860
tatgggggat gagtatgggc atacccgcta tggaaataat aacagttatg acatgatac     1920 cgccatcaac aatttccagt ggggacaatt ggaagcaagg aagaatgatc acttcaggtt    1980
cttttccaag atgataaagt ttcgactgtc ccacaatgtt cttagaaagg aaaacttcat    2040
tgagaagaac gacattacct ggctcgagga caactggtac aatgaagaga gtagattcct    2100
tgcatttatg ctccatgatg ggaatggagg agatatttac ttggcattta atgcacacca    2160
cttctccatc aaaacagcaa taccttcacc accacgaaat agaagttggt accgagtggt    2220
ggacactaat ctgaaatcac cagatgattt tgttactgag ggagtgtctg gtatcagtaa    2280
aacttatgat gttgcgccgt actctgctat ccttcttgaa gcaaagcaat aattaccggg    2340
actatgctgc tttagatgtt gtccatgagt tattacagta ttacctcctt ctggattgga    2400
tagttcaaat cggaattcag gctgttagcc tatagatgtt tgcaataagc aaccagtttg    2460
ttcaagctgc tattgacagg tacaaacacc ccatagtaat aagataaact gagaccattg    2520
atccaaaaaa aaaaaaaaaa aaaaaaaaaa aaaaaaaaaa aaaaaaaaaa aaaaaaaaaa    2580
aaaaaaaaaa aaaaaaaaaa aaaaaaaaaa aaaaaaaaaa aaaaaaaaaa aaaa           2634
```

<210> SEQ ID NO 4
<211> LENGTH: 878
<212> TYPE: PRT
<213> ORGANISM: Solanum tuberosum

<400> SEQUENCE: 4

```
Met Ala Thr Ser Pro Ile Gln Leu Ala Val His Ser Arg Leu Leu Ser
  1               5                  10                  15

Tyr Gly Ser Thr Glu Ser Thr Lys Leu Val Pro Ser Ser Ser Gly Asn
             20                  25                  30

Arg Gly Lys Ile Val Cys Ser Leu Arg Lys Leu Glu Leu Glu Asp Met
         35                  40                  45

Asn Phe Ser Gly Ile Gly Arg Asn Asn Asp Gln Glu Ala Pro Arg Arg
     50                  55                  60

Ala His Arg Arg Lys Ala Leu Ser Ala Ser Arg Ile Ser Leu Val Pro
 65                  70                  75                  80

Ser Ala Lys Arg Val Pro Thr Tyr Leu Phe Arg Thr Asp Ile Gly Gly
                 85                  90                  95

Gln Val Lys Val Leu Val Glu Arg Thr Asn Gly Lys Tyr Lys Val Leu
            100                 105                 110

Val Glu Val Leu Pro Leu Glu Leu Ser Tyr Ala His Ser Glu Leu Val
        115                 120                 125

Met Val Trp Gly Leu Phe Arg Ser Asp Ala Ser Cys Phe Met Pro Leu
    130                 135                 140

Asp Leu Asn Arg Arg Gly Ala Asp Gly Lys Ser Ser Thr Val Glu Thr
145                 150                 155                 160

Pro Phe Val Gln Gly Pro Ser Gly Lys Val Thr Val Glu Leu Asp Phe
                165                 170                 175

Glu Ala Ser Leu Ala Pro Phe Tyr Ile Ser Phe Tyr Met Lys Ser Gln
            180                 185                 190

Leu Val Ser Asp Met Glu Asn Ser Glu Ile Arg Ser His Arg Asn Thr
        195                 200                 205

Asn Phe Val Pro Val Gly Leu Ser Ser Gly His Pro Ala Pro Leu
    210                 215                 220
```

-continued

```
Gly Ile Ser Phe Gln Pro Asp Gly Ser Val Asn Phe Ala Leu Phe Ser
225                 230                 235                 240

Arg Ser Ala Arg Ser Val Val Leu Cys Leu Tyr Asp Asp Ile Ser Val
            245                 250                 255

Glu Lys Pro Ser Leu Glu Ile Asp Leu Asp Pro Tyr Ile Asn Arg Ser
        260                 265                 270

Gly Asp Ile Trp His Ala Ala Leu Asp Cys Ser Leu Pro Phe Lys Thr
    275                 280                 285

Tyr Gly Tyr Arg Cys Lys Ala Thr Thr Ser Gly Lys Gly Glu Leu Val
290                 295                 300

Leu Leu Asp Pro Tyr Ala Lys Val Ile Arg Arg Val Ile Pro Arg Gln
305                 310                 315                 320

Gly Gly Ser Glu Ile Arg Pro Lys Tyr Leu Gly Glu Leu Cys Leu Glu
            325                 330                 335

Pro Gly Tyr Asp Trp Ser Gly Asp Val Pro Pro Ser Leu Pro Met Glu
        340                 345                 350

Lys Leu Ile Ile Tyr Arg Leu Asn Val Thr Gln Phe Thr Lys Asp Lys
    355                 360                 365

Ser Ser Lys Leu Pro Asp Asp Leu Ala Gly Thr Phe Ser Gly Ile Ser
370                 375                 380

Glu Lys Trp His His Phe Lys Asp Leu Gly Val Asn Ala Met Leu Leu
385                 390                 395                 400

Glu Pro Ile Phe Pro Phe Asp Glu Gln Lys Gly Pro Tyr Phe Pro Trp
            405                 410                 415

His Phe Phe Ser Pro Gly Asn Met Tyr Gly Pro Ser Gly Asp Pro Leu
        420                 425                 430

Ser Ala Ile Lys Ser Met Lys Asp Met Val Lys Lys Leu His Ala Asn
            435                 440                 445

Gly Ile Glu Val Phe Leu Glu Val Val Phe Thr His Thr Ala Glu Asp
    450                 455                 460

Ala Pro Leu Met Asn Val Asp Asn Phe Ser Tyr Cys Ile Lys Gly Gly
465                 470                 475                 480

Gln Tyr Leu Asn Ile Gln Asn Ala Leu Asn Cys Asn Tyr Pro Ile Val
            485                 490                 495

Gln Gln Met Ile Leu Asp Cys Leu Arg His Trp Val Ile Glu Phe His
        500                 505                 510

Ile Asp Gly Phe Val Phe Val Asn Ala Ser Ser Leu Leu Arg Gly Phe
    515                 520                 525

Asn Gly Glu Ile Leu Ser Arg Pro Pro Leu Val Glu Ala Ile Ala Phe
530                 535                 540

Asp Pro Ile Leu Ser Lys Val Lys Met Ile Ala Asp Asn Trp Asn Pro
545                 550                 555                 560

Leu Thr Asn Asp Ser Lys Glu Asn Leu Phe Pro His Trp Arg Arg Trp
            565                 570                 575

Ala Glu Ile Asn Met Arg Phe Cys Asp Asp Ile Arg Asp Phe Leu Arg
        580                 585                 590

Gly Glu Gly Leu Leu Ser Asn Leu Ala Thr Arg Leu Cys Gly Ser Gly
            595                 600                 605

Asp Ile Phe Ala Gly Gly Arg Gly Pro Ala Phe Ser Phe Asn Tyr Ile
    610                 615                 620

Ala Arg Asn Ser Gly Leu Thr Leu Val Asp Leu Val Ser Phe Ser Ser
625                 630                 635                 640
```

```
Asn Glu Val Ala Ser Glu Leu Ser Trp Asn Cys Gly Gln Gly Ala
                645                 650                 655

Thr Thr Asn Asn Ile Val Leu Glu Arg Arg Leu Lys Gln Val Arg Asn
            660                 665                 670

Phe Leu Phe Ile Leu Phe Ile Ser Leu Gly Val Pro Val Leu Asn Met
            675                 680                 685

Gly Asp Glu Cys Gly Gln Ser Ser Gly Gly Pro Pro Ala Tyr Asp Ala
    690                 695                 700

Arg Lys Ser Leu Gly Trp Asn Thr Leu Lys Thr Gly Phe Gly Thr Gln
705                 710                 715                 720

Ile Ala Gln Phe Ile Ser Phe Leu Ser Asn Leu Arg Met Arg Arg Ser
                725                 730                 735

Asp Leu Leu Gln Lys Arg Thr Phe Leu Lys Glu Asn Ile Gln Trp
            740                 745                 750

His Gly Ser Asp Gln Ser Pro Pro Lys Trp Asp Gly Pro Ser Ser Lys
            755                 760                 765

Phe Leu Ala Met Thr Leu Lys Ala Asp Ala Glu Val Ser Gln Thr Leu
    770                 775                 780

Val Ser Asp Ile Val Gly Asp Leu Phe Val Ala Phe Asn Gly Ala Gly
785                 790                 795                 800

Asp Ser Glu Ile Val Ile Leu Pro Pro Pro Thr Asp Met Val Trp
                805                 810                 815

His Arg Leu Val Asp Thr Ala Leu Pro Phe Pro Gly Phe Phe Asp Glu
            820                 825                 830

Lys Gly Thr Pro Val Glu Asp Glu Leu Val Ala Tyr Glu Met Lys Ser
            835                 840                 845

His Ser Cys Leu Leu Phe Glu Ala Gln Arg Leu Ala Glu Ile Asp Ser
    850                 855                 860

Ser Lys Arg Lys Lys Gln Ile Arg Leu Ser Ser Lys Arg Gln
865                 870                 875

<210> SEQ ID NO 5
<211> LENGTH: 793
<212> TYPE: PRT
<213> ORGANISM: Solanum tuberosum

<400> SEQUENCE: 5

Met Glu Leu Leu His Cys Pro Ser Ile Ser Thr Tyr Lys Pro Lys Leu
1               5                   10                  15

Ser Phe His Asn His Leu Phe Ser Arg Arg Ser Ser Asn Gly Val Asp
            20                  25                  30

Phe Glu Ser Ile Trp Arg Lys Ser Arg Ser Ser Val Val Asn Ala Ala
        35                  40                  45

Val Asp Ser Gly Arg Gly Gly Val Val Lys Thr Ala Ala Thr Ala Val
    50                  55                  60

Val Val Glu Lys Pro Thr Thr Glu Arg Cys Arg Phe Glu Val Leu Ser
65                  70                  75                  80

Gly Lys Pro Leu Pro Phe Gly Ala Thr Thr Asp Gly Gly Val Asn
                85                  90                  95

Phe Ala Val Phe Ser Arg Asn Ala Thr Ala Ala Thr Leu Cys Leu Ile
            100                 105                 110

Thr Leu Ser Asp Leu Pro Glu Lys Arg Val Thr Glu Gln Ile Phe Leu
        115                 120                 125

Asp Pro Leu Ala Asn Lys Thr Gly Asp Val Trp His Val Phe Leu Lys
    130                 135                 140
```

```
Gly Asp Phe Glu Asn Met Leu Tyr Gly Tyr Lys Phe Asp Gly Lys Phe
145                 150                 155                 160

Cys Pro Glu Glu Gly His Tyr Phe Asp Ser Ser Gln Ile Val Leu Asp
                165                 170                 175

Pro Tyr Ala Lys Ala Ile Val Ser Arg Gly Glu Tyr Gly Val Leu Gly
            180                 185                 190

Pro Glu Asp Asp Cys Trp Pro Pro Met Ala Gly Met Val Pro Ser Ala
        195                 200                 205

Ser Asp Gln Phe Asp Trp Glu Gly Asp Leu Pro Leu Lys Phe Pro Gln
210                 215                 220

Arg Asp Leu Val Ile Tyr Glu Met His Val Arg Gly Phe Thr Asn His
225                 230                 235                 240

Glu Ser Ser Glu Thr Lys Tyr Pro Gly Thr Tyr Leu Gly Val Val Glu
                245                 250                 255

Lys Leu Asp His Leu Lys Glu Leu Gly Val Asn Cys Ile Glu Leu Met
                260                 265                 270

Pro Cys His Glu Phe Asn Glu Leu Glu Tyr Tyr Ser Tyr Asn Ser Val
            275                 280                 285

Leu Gly Asp Tyr Lys Phe Asn Phe Trp Gly Tyr Ser Thr Val Asn Phe
290                 295                 300

Phe Ser Pro Met Gly Arg Tyr Ser Ser Ala Gly Leu Ser Asn Cys Gly
305                 310                 315                 320

Leu Gly Ala Ile Asn Glu Phe Lys Tyr Leu Val Lys Glu Ala His Lys
                325                 330                 335

Arg Gly Ile Glu Val Ile Met Asp Val Val Phe Asn His Thr Ala Glu
                340                 345                 350

Gly Asn Glu Asn Gly Pro Ile Leu Ser Phe Arg Gly Ile Asp Asn Ser
                355                 360                 365

Val Phe Tyr Thr Leu Ala Pro Lys Gly Glu Phe Tyr Asn Tyr Ser Gly
            370                 375                 380

Cys Gly Asn Thr Phe Asn Cys Asn Asn Pro Ile Val Arg Gln Phe Ile
385                 390                 395                 400

Val Asp Cys Leu Arg Tyr Trp Val Thr Glu Met His Val Asp Gly Phe
                405                 410                 415

Arg Phe Asp Leu Ala Ser Ile Leu Thr Arg Ser Ser Ser Ser Trp Asn
                420                 425                 430

Ala Val Asn Val Tyr Gly Asn Ser Ile Asp Gly Asp Val Ile Thr Thr
            435                 440                 445

Gly Thr Pro Leu Thr Ser Pro Pro Leu Ile Asp Met Ile Ser Asn Asp
450                 455                 460

Pro Ile Leu Arg Gly Val Lys Leu Ile Ala Glu Ala Trp Asp Cys Gly
465                 470                 475                 480

Gly Leu Tyr Gln Val Gly Met Phe Pro His Trp Gly Ile Trp Ser Glu
                485                 490                 495

Trp Asn Gly Lys Tyr Arg Asp Met Val Arg Gln Phe Ile Lys Gly Thr
                500                 505                 510

Asp Gly Phe Ser Gly Ala Phe Ala Glu Cys Leu Cys Gly Ser Pro Asn
            515                 520                 525

Leu Tyr Gln Lys Gly Gly Arg Lys Pro Trp Asn Ser Ile Asn Phe Val
            530                 535                 540

Cys Ala His Asp Gly Phe Thr Leu Ala Asp Leu Val Thr Tyr Asn Asn
545                 550                 555                 560
```

```
Lys His Asn Leu Ala Asn Gly Glu Asp Asn Lys Asp Gly Glu Asn His
            565                 570                 575

Asn Asn Ser Trp Asn Cys Gly Glu Glu Gly Glu Phe Ala Ser Ile Phe
        580                 585                 590

Val Lys Lys Leu Arg Lys Arg Gln Met Arg Asn Phe Phe Leu Cys Leu
            595                 600                 605

Met Val Ser Gln Gly Val Pro Met Ile Tyr Met Gly Asp Glu Tyr Gly
    610                 615                 620

His Thr Lys Gly Gly Asn Asn Thr Tyr Cys His Asp Asn Tyr Ile
625                 630                 635                 640

Asn Tyr Phe Arg Trp Asp Lys Lys Asp Glu Ser Ser Asp Phe Leu
                645                 650                 655

Arg Phe Cys Gly Leu Met Thr Lys Phe Arg His Glu Cys Glu Ser Leu
            660                 665                 670

Gly Leu Asp Gly Phe Pro Thr Ala Glu Arg Leu Gln Trp His Gly His
            675                 680                 685

Thr Pro Arg Thr Pro Asp Trp Ser Glu Thr Ser Arg Phe Val Ala Phe
        690                 695                 700

Thr Leu Val Asp Lys Val Lys Gly Glu Leu Tyr Ile Ala Phe Asn Ala
705                 710                 715                 720

Ser His Leu Pro Val Thr Ile Thr Leu Pro Asp Arg Pro Gly Tyr Arg
                725                 730                 735

Trp Gln Pro Phe Val Asp Thr Gly Lys Pro Ala Pro Phe Asp Phe Leu
            740                 745                 750

Thr Asp Asp Val Pro Glu Arg Glu Thr Ala Ala Lys Gln Tyr Ser His
                755                 760                 765

Phe Leu Asp Ala Asn Gln Tyr Pro Met Leu Ser Tyr Ser Ser Ile Ile
            770                 775                 780

Leu Leu Leu Ser Ser Ala Asp Asp Ala
785                 790

<210> SEQ ID NO 6
<211> LENGTH: 766
<212> TYPE: PRT
<213> ORGANISM: Solanum tuberosum

<400> SEQUENCE: 6

Met Ile Arg Gly Pro Pro Gln Ile Val Gln Lys Cys Pro Thr Asp Ile
  1               5                  10                  15

Val Thr Val Asn Arg Thr Asn Ile Val Pro Arg Thr His Arg His Ala
             20                  25                  30

Leu Gln Asp Leu Arg Gln Leu Arg Arg Arg Asp Ser Leu Arg Leu Phe
         35                  40                  45

Ser Ser Asp His Arg Ile Leu Lys Phe Cys Thr Ser Glu Glu Ala Phe
     50                  55                  60

Gln Pro Arg Leu Val Ala Ala Lys Leu Gln Glu Glu Ala Pro Gln
 65                  70                  75                  80

Met Leu Asp Thr Phe Pro Ser Phe Lys Val Ser Pro Gly Leu Ala His
                 85                  90                  95

Pro Leu Gly Val Ser Glu Thr Ser Gly Ile Asn Phe Ala Ile Phe
            100                 105                 110

Ser Gln His Ala Ser Ala Val Thr Leu Cys Ile Ile Leu Pro Lys Ser
        115                 120                 125

Val His Asp Gly Met Ile Glu Leu Ala Leu Asp Pro Gln Lys Asn Arg
    130                 135                 140
```

-continued

```
Thr Gly Asp Ile Trp His Ile Cys Ile Lys Glu Leu Pro Gln Gly Gly
145                 150                 155                 160

Val Leu Tyr Gly Tyr Arg Ile Asp Gly Pro Arg Asn Trp His Glu Gly
            165                 170                 175

His Arg Phe Asp Asp Ser Ile Ile Leu Val Asp Pro Tyr Ala Lys Leu
            180                 185                 190

Ile Glu Gly Arg Arg Val Phe Gly Asp Glu Ser Asn Lys Met Cys Arg
            195                 200                 205

Phe Phe Gly Thr Tyr Asp Phe Asn Ser Leu Pro Phe Asp Trp Gly Glu
            210                 215                 220

Asn Tyr Lys Leu Pro Asn Ile Pro Glu Lys Asp Leu Val Ile Tyr Glu
225                 230                 235                 240

Met Asn Val Arg Ala Phe Thr Ala Asp Glu Thr Ser Ser Leu Asp Gln
                245                 250                 255

Asp Gln Arg Gly Ser Tyr Leu Gly Leu Ile Glu Lys Ile Pro His Leu
            260                 265                 270

Leu Glu Leu Gly Val Asn Ala Val Glu Leu Leu Pro Val Phe Glu Phe
            275                 280                 285

Asp Glu Leu Glu Leu Gln Arg Arg Pro Asn Pro Arg Asp His Met Ile
290                 295                 300

Asn Thr Trp Gly Tyr Ser Thr Ile Asn Phe Phe Ala Pro Met Ser Arg
305                 310                 315                 320

Tyr Ala Ser Cys Gly Gly Pro Val Arg Ala Ser Trp Glu Phe Lys
                325                 330                 335

Glu Met Val Lys Ala Leu His Gly Ala Gly Ile Glu Val Ile Leu Asp
            340                 345                 350

Val Val Tyr Asn His Thr Asn Glu Ala Asp Asp Glu Asn Pro Tyr Thr
            355                 360                 365

Thr Ser Phe Arg Gly Ile Asp Asn Lys Val Tyr Met Val Asp Leu
            370                 375                 380

Asn Asn Asn Ala Gln Leu Leu Asn Phe Ala Gly Cys Gly Asn Thr Phe
385                 390                 395                 400

Asn Cys Asn His Pro Thr Val Met Glu Leu Ile Leu Glu Ser Leu Arg
                405                 410                 415

His Trp Val Thr Glu Tyr His Val Asp Gly Phe Arg Phe Asp Leu Ala
            420                 425                 430

Ser Val Leu Cys Arg Gly Thr Asp Gly Thr Pro Ile Asn Ala Pro Pro
            435                 440                 445

Leu Val Lys Ala Ile Ser Lys Asp Ser Val Leu Ser Arg Cys Lys Ile
450                 455                 460

Ile Ala Glu Pro Trp Asp Cys Gly Gly Leu Tyr Leu Val Gly Lys Phe
465                 470                 475                 480

Pro Asn Trp Asp Arg Trp Ala Glu Trp Asn Gly Lys Tyr Arg Asp Asp
            485                 490                 495

Ile Arg Arg Phe Ile Lys Gly Asp Ala Gly Met Lys Gly Asn Phe Ala
            500                 505                 510

Thr Arg Ile Ala Gly Ser Ala Asp Leu Tyr Arg Val Asn Lys Arg Lys
            515                 520                 525

Pro Tyr His Ser Val Asn Phe Val Ile Ala His Asp Gly Phe Thr Leu
            530                 535                 540

Tyr Asp Leu Val Ser Tyr Asn Asn Lys His Asn Asp Ala Asn Gly Glu
545                 550                 555                 560
```

```
Gly Gly Asn Asp Gly Cys Asn Asp Asn Phe Ser Trp Asn Cys Gly Ile
            565                 570                 575
Glu Gly Glu Thr Ser Asp Ala Asn Ile Asn Ala Leu Arg Ser Arg Gln
            580                 585                 590
Met Lys Asn Phe His Leu Ala Leu Met Val Ser Gln Gly Thr Pro Met
            595                 600                 605
Met Leu Met Gly Asp Glu Tyr Gly His Thr Arg Tyr Gly Asn Asn
        610                 615                 620
Ser Tyr Gly His Asp Thr Ala Ile Asn Asn Phe Gln Trp Gly Gln Leu
625                 630                 635                 640
Glu Ala Arg Lys Asn Asp His Phe Arg Phe Phe Ser Lys Met Ile Lys
            645                 650                 655
Phe Arg Leu Ser His Asn Val Leu Arg Lys Glu Asn Phe Ile Glu Lys
            660                 665                 670
Asn Asp Ile Thr Trp Leu Glu Asp Asn Trp Tyr Asn Glu Glu Ser Arg
            675                 680                 685
Phe Leu Ala Phe Met Leu His Asp Gly Asn Gly Gly Asp Ile Tyr Leu
            690                 695                 700
Ala Phe Asn Ala His His Phe Ser Ile Lys Thr Ala Ile Pro Ser Pro
705                 710                 715                 720
Pro Arg Asn Arg Ser Trp Tyr Arg Val Val Asp Thr Asn Leu Lys Ser
            725                 730                 735
Pro Asp Asp Phe Val Thr Glu Gly Val Ser Gly Ile Ser Lys Thr Tyr
            740                 745                 750
Asp Val Ala Pro Tyr Ser Ala Ile Leu Leu Glu Ala Lys Gln
            755                 760                 765

<210> SEQ ID NO 7
<211> LENGTH: 428
<212> TYPE: DNA
<213> ORGANISM: Artificial Sequence
<220> FEATURE:
<223> OTHER INFORMATION: Description of Artificial Sequence: Probe
<221> NAME/KEY: misc_feature
<222> LOCATION: (83, 189, 200, 272, 315, 329, 335, 366, 369, 381-383,
      390, 402, 404 and 425)
<223> OTHER INFORMATION: n = a or g or c or t

<400> SEQUENCE: 7
agtagttttt acacatactg ctgattctgg agctcttcgt ggaattgatg acagttccta      60
ttactacaag ggaagagcca atnatctaga ttctaaaagt tacttgaact gtaactatcc     120
tgttgttcag cagttggtat tggagagctt gcgttattgg gtaaccgagt ttcatgtaga     180
tggattttnt tttataaatn cttcatctct cttgagaggc gttcacggtg aacagctctc     240
tcgtcctcct ttggttgaag caatagcttt tnatccactt cttgcggaga ccaaactaat     300
agctgattgc tgggntccac ttgaaatgnt gccanaagaa gtacgggttc ccacaatttg     360
gaagcnatng gcagaactca nnncaaggtn ttttcgaaa tntnaggaaa ttttttaagg     420 ggaangggg                                                             428

<210> SEQ ID NO 8
<211> LENGTH: 38
<212> TYPE: PRT
<213> ORGANISM: Solanum tuberosum

<400> SEQUENCE: 8

Met Ala Thr Ser Pro Ile Gln Leu Ala Val His Ser Arg Leu Leu Ser
  1               5                  10                  15
```

```
Tyr Gly Ser Thr Glu Ser Thr Lys Leu Val Pro Ser Ser Ser Gly Asn
            20                  25                  30

Arg Gly Lys Ile Val Cys
        35

<210> SEQ ID NO 9
<211> LENGTH: 47
<212> TYPE: PRT
<213> ORGANISM: Solanum tuberosum

<400> SEQUENCE: 9

Met Glu Leu Leu His Cys Pro Ser Ile Ser Thr Tyr Lys Pro Lys Leu
 1               5                  10                  15

Ser Phe His Asn His Leu Phe Ser Arg Arg Ser Ser Asn Gly Val Asp
            20                  25                  30

Phe Glu Ser Ile Trp Arg Lys Ser Arg Ser Ser Val Val Asn Ala
            35                  40                  45

<210> SEQ ID NO 10
<211> LENGTH: 2843
<212> TYPE: DNA
<213> ORGANISM: Solanum tuberosum
<220> FEATURE:
<221> NAME/KEY: misc_feature
<222> LOCATION: (1868, 1876)
<223> OTHER INFORMATION: n = a or g or c or t

<400> SEQUENCE: 10
cttatgggac ttgattaaga atatgtgatc caccaagttc tatatctgac gctgttgtaa      60
cattgtgtgc tgctaatggc aacttcacca atacagttgg ctgtgcattc acgtttgttg     120
agctatggca gtactgagtc aaccaagttg gttccttcat catcaggtaa ccgtggaaaa     180
atagtatgca gtctaaggaa gctggaattg aagacatga atttctctgg cataggtcga     240
aataatgatc aagaagctcc taggagagct catcgacgaa aagcactatc agcatcgaga     300
atttcgcttg ttccatctgc aaaaagggtt cccacttacc ttttcaggac agatattggt     360
ggtcaagtga agtcttggt ggaaaagaca aatggaaagt acaaagtgct tgtagaagtc     420
ttgccattgg agctctcaga tgcacattct gagctagtta tggtttgggg cttttttaga     480
tctgatgctt tatgctttat gcctctggat ctaaacagac gtggagcaga tggaaaaagt     540
agtactgttg aaacaccatt tgtgcaagga ccttcaggca aggtcaccgt ggagctggat     600
tttgaagcaa gtttagcccc cttctatatc tccttctata tgaagtcaca actagtttct     660
gacatggaaa actcagaaat cagaagtcac aggaacacaa attttgttgt accagttggt     720
ctcagttcag ggcatcctgc tccattgggt atttcctttc agccagatgg atctgtgaat     780
tttgctctct tctcacgcag tgcaagaagt gtagttctgt gcttgtatga tgacatatca     840
gttgaaaaac cttctttaga gattgatcta gatccttata ttaatcgatc aggcgatatt     900
tggcatgctg ctttagattg ttcttttgcca tttaagactt atggttatag atgtaaggcg     960
actacttctg ggaagggaga gctggttctt ttggacccat atgctaaggt gataaggcgt    1020
gttattcctc gtcagggtgg gtctgagata cgtccaaaat atcttggaga actatgcctg    1080
gaacctggct atgattggag cggtgatgtc ccccctagct tacctatgga gaaactaata    1140
atttaccgct taaatgtgac tcaatttaca aggacaagt ccagtaagct acctgatgac    1200
cttgctggaa ctttctctgg cattagcgaa aaatggcacc attttaaaga tcttggtgtg    1260
aatgcaatgt tactggagcc aatttttccct tttgatgagc agaaaggacc ctattttccg    1320
```

```
tggcatttct tttcacctgg aaatatgtat ggaccttctg gtgaccctct ttctgccatt      1380
aaatcgatga aggatatggt taagaaatta catgctaacg ggatagaggt ttttcttgaa      1440
gttgttttca ctcacactgc agaggatgca cctttgatga atgttgataa cttttcatat      1500
tgcataaaag gtggtcagta tctgaatatt caaaatgcat tgaattgcaa ttaccccata      1560
gtccaacaaa tgattttgga ctgtctccgc cactgggtaa ttgagtttca tattgatggt      1620
tttgtttttg tcaacgcttc ttccttgttg agagggttca atggagagat tctatctcgt      1680
cctccattag ttgaagctat tgcctttgat cctatccttt caaaggtcaa gatgattgca      1740
gataattgga atccattaac caatgattcg aaggaaaatt tattccctca ctggaggaga      1800
tgggcagaga taaatgag attttgtgat gacattcgag acttcttgag aggcgagggt      1860
cttctaanca atctancaac acgactttgt ggaagtgggg atatcttcgc aggtggacgt      1920
ggtcctgcat tctcttttaa ttatattgcc agaaattctg gactcacact tgttgaccta      1980
gttagcttca gtagtaatga agtggcttca gagttaagtt ggaactgtgg acaagaaggc      2040
gctacgacca ataacattgt cctagagaga cgacttaaac aagttcgtaa ttttctgttc      2100
atattgttca tttctctagg tgtaccagta cttaacatgg gagacgagtg tggtcagtct      2160
tcaggaggtc cccctgcata tgatgctcga aaatctttgg gttggaatac tttaaaaact      2220
ggttttggga ctcagattgc ccagtttatt tcattcttga gtaatttaag aatgagaaga      2280
agtgatcttc ttcaaaagag aaccttcttg aaggaagaaa acatccagtg gcatgggagt      2340
gaccaatctc ctccgaaatg ggatggcccg tctagcaaat tcttggctat gactttgaag      2400
gccgatgctg aagtcagcca gacattagtc tctgatatcg taggtgacct gtttgttgct      2460
ttcaatggtg ctggtgattc agagattgtt atccttccac ctcctccaac agatatggta      2520
tggcatcgtc tcgttgacac agccctccct ttcccggggt ttttcgatga aagggaact      2580 ccagttgaag atgaattagt tgcttatgag atgaagtctc acagctgttt gctgtttgaa      2640
gctcagagac tagctgaaat agattctagc aagagaaaga aacagattag actttcttct      2700
aagaggcaat agtttgtaaa gcccctaagt atatatatat gtttaaataa gaggcttttt      2760
tttctgaata aataagaaga ttttactgag aatacttgta tctaaacatt ttcttttgca      2820
gcttcaaata aaaaaaaaaa aaa                                              2843
```

<210> SEQ ID NO 11
<211> LENGTH: 2806
<212> TYPE: DNA
<213> ORGANISM: Solanum tuberosum
<220> FEATURE:
<221> NAME/KEY: misc_feature
<222> LOCATION: (822, 826, 2707 and 2797)
<223> OTHER INFORMATION: n = a or g or c or t

<400> SEQUENCE: 11

```
ggcggccgct ctagaactag tggatccccc gggctgcagg aattcgagga tccgggtacc       60
atggctcagt ccttctcaat ttcagtgcca catactctag atcacactct ctctcttcct      120
caaagttctc ccatggagtt acttcattgt ccttccattt ctacctacaa acctaaactc      180
tctttccaca accatctttt ctcgaggaga agcagtaacg tgtagatttt tgagagtatt      240
tggagaaaat cgaggtcttc agtggttaat gctgctgttg atagtggacg tggaggtgtg      300
gtgaagactg cggctactgc ggtggtggtg gagaagccga cgacggaacg atgtcgtttg      360
aggttttatc agggaaagcc attgccgttt ggtgctactg cgacagatgg tggtgtgaat      420
```

-continued

| | |
|---|---|
| ttcgctgttt ttcaaggaaa tgctacagct gctactcttt gcttgatcac tctttccgat | 480 |
| ttacctgaga agagagtgac cgagcaaatt ttcctggatc ctctagctaa taaaactgga | 540 |
| gatgtatggc atgtgttcct taagggagat tttgagaata tgctatatgg ctacaaattt | 600 |
| gatgggaaat tctgtcctga agaaggacac tactttgact cttcgcagat agtgttggat | 660 |
| ccttatgcca aggctatagt aagcagagga gaatatggtg tattagggcc agaggatgat | 720 |
| tgttggcccc caatggctgg catggtaccc ttctgcttct ggatcagttt gtattgggaa | 780 |
| ggagatctac cactggaagt ttcccacaga gagatcttgt tnatcnatga aatgcatgtt | 840 |
| cgtgggttta ctatccatga gtcgagtgaa acaaaatatc ctggtactta ccttggtgtt | 900 |
| gtggagaaac ttgatcactt gaaggaactt ggtgtcaact gtatagagct aatgccctgt | 960 |
| cacgagttca atgagctgga gtactatagt tataactctg tattgggcga ctacaagttt | 1020 |
| aacttttggg gctattctac tgtcaatttc ttttctccaa tgggaagata ctcatctgct | 1080 |
| ggtctaagta attgcggcct cggtgcaata aacgaattta agtatcttgt caaggaagca | 1140 |
| cataaacgtg gaatcgaggt tatcatggat gttgttttca atcacactgc tgaaggaaat | 1200 |
| gaaaatggtc ccatactatc atttagaggc attgacaaca gtgtgtttta tacgctagct | 1260 |
| cctaaggggt aattttacaa ctactccagga tgtggaaata ccttcaactg taataatccc | 1320 |
| attgtacgtc aatttatagt gatgctgaga tattgggtta ccgaaatgca cgtacatggc | 1380 |
| ttccgctttg atcttgcttc tatccttaca agaagtagca gctcgtggaa tgctgtaaat | 1440 |
| gtctatggaa attcaattga cggtgacgtg atcaccacag gcactcctct cacaagccca | 1500 |
| ccattgattg atatgattag caatgatcca atacttcgtg gagtaaagct tatagctgaa | 1560 |
| gcatgggatt gtggaggcct ttaccaagtt ggcatgtttc cgcactgggg tatctggtcg | 1620 |
| gagtggaacg gaaagtaccg tgacatggta cggcagttca tcaaaggcac tgatgggttt | 1680 |
| tctggggctt tgctgaatg cctttgtgga agcccaaatc tataccagaa aggaggaaga | 1740 |
| aaaccatgga acagtataaa tttcgtgtgt gcccacgatg gttttacttt ggctgattta | 1800 |
| gtgacataca acaataaaca caatttggca aatggagagg acaacaaaga cggggagaat | 1860 |
| cacaataata gttggaattg tggtgaggaa ggagaatttg caagtatctt tgtgaagaaa | 1920 |
| ttgaggaaaa gacaaatgcg gaacttcttc ctctgcctta tggtttccca aggtgttccc | 1980 |
| atgatatata tgggcgatga atatggtcac actaagggag gaaacaacaa cacgtattgc | 2040 |
| catgataatt atattaatta cttccgttgg gataagaagg atgaatcttc atctgatttt | 2100 |
| ttgagatttt gcggcctcat gaccaaattc cgccatgaat gtgaatcact gggattagat | 2160 |
| ggtttcccta cagcagaaag gctgcaatgg catggtcaca ctcctagaac tccagattgg | 2220 |
| tctgaaacaa gtcgattcgt tgcattcaca ctggtcgaca aagtgaaggg agaactatat | 2280 |
| attgccttta acgccagcca tttgcctgta acgattacac ttccagatag gcctggttat | 2340 |
| agatggcagc cgtttgtgga cacaggcaaa ccagcaccat ttgacttctt gacagacgac | 2400 |
| gttcctgaga gagagacagc agccaaacaa tattctcatt ttctggacgc gaaccagtat | 2460 |
| ccgatgctca gttattcatc cattattctt ttactatcat ctgctgatga tgcatagttt | 2520 |
| cattcaccaa gttaggtgga ggtaaatcag cttcagattt tgttatatgc agtgaggtgt | 2580 |
| tactttgtaa ataaaagtaa gaagcaggac agaacagaac tgcaaacgga taaaatttgt | 2640 |
| gaggaagaag ctgatgattt ataagataca ccttgtattt taattgcatt tatataaaat | 2700 |
| aaaatantag tgaaattgtc tgtgcgaaaa aaaaaaaaaa aaaaaataaa aaaaaaaaaa | 2760 |
| aaaaaaaaaa aaccatggta cccggatcct cgaattngat atcaag | 2806 |

<210> SEQ ID NO 12
<211> LENGTH: 1389
<212> TYPE: DNA
<213> ORGANISM: Solanum tuberosum

<400> SEQUENCE: 12

| | | | | | | |
|---|---|---|---|---|---|---|
| ctcattccga | ggaatagaca | acaaggttta | ttacatggta | gatttgaaca | acaatgctca | 60 |
| gctgctgaat | ttcgctggat | gtggaaatac | ttttaactgc | aatcatccta | cagtcatgga | 120 |
| acttatactt | gaaagcttaa | gacactgggt | caccgagtat | catgtcgatg | gatttcgctt | 180 |
| tgatcttgct | agtgttcttt | gcagagggac | agatggtact | cccattaatg | ctccccccct | 240 |
| tgtaaaggcc | atttccaaag | atagtgtatt | gtcgaggtgc | aaaattattg | ctgagccatg | 300 |
| ggattgtgga | ggcctatatc | ttgttggaaa | gtttccgaac | tgggaccggt | gggctgagtg | 360 |
| gaatgggaag | taccgcgatg | acatcaggag | atttataaag | ggcgatgctg | gcatgaaagg | 420 |
| aaattttgca | acccgtatcg | caggttcagc | ggatctgtac | agagtgaaca | agcgaaagcc | 480 |
| gtaccacagt | gtcaacttcg | tgattgccca | tgatggcttt | accttgtatg | accttgtttc | 540 |
| atacaataat | aagcacaatg | atgcgaacgg | tgaaggtggc | aatgatggat | gcaatgacaa | 600 |
| cttcagttgg | aattgtggaa | ttgaaggtga | aacttcagat | gcaaatatta | acgcactgcg | 660 |
| ttcacggcaa | atgaaaaatt | ttcatttggc | actgatggtt | tctcagggaa | caccaatgat | 720 |
| gcttatgggg | gatgagtatg | ggcatacccg | ctatggaaat | aataacagtt | atggacatga | 780 |
| taccgccatc | aacaatttcc | agtggggaca | attggaagca | aggaagaatg | atcacttcag | 840 |
| gttcttttcc | aagatgataa | agtttcgact | gtcccacaat | gttcttagaa | aggaaaactt | 900 |
| cattgagaag | aacgacatta | cctggctcga | ggacaactgg | tacaatgaag | agagtagatt | 960 |
| ccttgcattt | atgctccatg | atgggaatgg | aggagatatt | tacttggcat | ttaatgcaca | 1020 |
| ccacttttcc | atcaaaacag | caataccttc | accaccacga | aatagaagtt | ggtaccgagt | 1080 |
| ggtggacact | aatctgaagt | caccagatga | ttttgttatt | gagggagtgt | ctggtatcag | 1140 |
| tgaaacttat | gatgttgcgc | cgtactctgc | tatccttctt | gaagcaaagc | aataattacc | 1200 |
| gggactatgc | tgctttagat | gttgtccatg | tgttattaca | gtattacctc | cttctggatt | 1260 |
| ggatagttca | aattggaatt | caggctgtta | gcctatagat | gtagtatgtt | gagcagaaat | 1320 |
| tttgcaataa | gcaaccagtt | ttgttcaaaa | aaaaaaaaaa | aaaaaaaaaa | aaaaaaaaaa | 1380 |
| aaaaaaaaa | | | | | | 1389 |

<210> SEQ ID NO 13
<211> LENGTH: 5
<212> TYPE: PRT
<213> ORGANISM: Solanum tuberosum

<400> SEQUENCE: 13

Leu Met Gly Leu Asp
 1               5

<210> SEQ ID NO 14
<211> LENGTH: 838
<212> TYPE: PRT
<213> ORGANISM: Solanum tuberosum
<220> FEATURE:
<221> NAME/KEY: SITE
<222> LOCATION: (274, 276)
<223> OTHER INFORMATION: Xaa = unknown amino acid

<400> SEQUENCE: 14

-continued

```
Gly Gly Arg Ser Arg Thr Ser Gly Ser Pro Gly Leu Gln Glu Phe Glu
 1               5                  10                  15

Asp Pro Gly Thr Met Ala Gln Ser Phe Ser Ile Ser Val Pro His Thr
             20                  25                  30

Leu Asp His Thr Leu Ser Leu Pro Gln Ser Ser Pro Met Glu Leu Leu
             35                  40                  45

His Cys Pro Ser Ile Ser Thr Tyr Lys Pro Lys Leu Ser Phe His Asn
             50                  55                  60

His Leu Phe Ser Arg Arg Ser Ser Asn Gly Val Asp Phe Glu Ser Ile
 65                  70                  75                  80

Trp Arg Lys Ser Arg Ser Ser Val Val Asn Ala Ala Val Asp Ser Gly
                 85                  90                  95

Arg Gly Gly Val Val Lys Thr Ala Ala Thr Ala Val Val Glu Lys
                100                 105                 110

Pro Thr Thr Glu Arg Cys Arg Leu Arg Phe Tyr Gln Gly Lys Pro Leu
             115                 120                 125

Pro Phe Gly Ala Thr Ala Thr Asp Gly Val Asn Phe Ala Val Phe
             130                 135                 140

Gln Gly Asn Ala Thr Ala Ala Thr Leu Cys Leu Ile Thr Leu Ser Asp
145                 150                 155                 160

Leu Pro Glu Lys Arg Val Thr Glu Gln Ile Phe Leu Asp Pro Leu Ala
                165                 170                 175

Asn Lys Thr Gly Asp Val Trp His Val Phe Leu Lys Gly Asp Phe Glu
                180                 185                 190

Asn Met Leu Tyr Gly Tyr Lys Phe Asp Gly Lys Phe Cys Pro Glu Glu
            195                 200                 205

Gly His Tyr Phe Asp Ser Ser Gln Ile Val Leu Asp Pro Tyr Ala Lys
            210                 215                 220

Ala Ile Val Ser Arg Gly Glu Tyr Gly Val Leu Gly Pro Glu Asp Asp
225                 230                 235                 240

Cys Trp Pro Pro Met Ala Gly Met Val Pro Phe Cys Phe Trp Ile Ser
                245                 250                 255

Leu Tyr Trp Glu Gly Asp Leu Pro Leu Glu Val Ser His Arg Glu Ile
                260                 265                 270

Leu Xaa Ile Xaa Glu Met His Val Arg Gly Phe Thr Ile His Glu Ser
        275                 280                 285

Ser Glu Thr Lys Tyr Pro Gly Thr Tyr Leu Gly Val Val Glu Lys Leu
            290                 295                 300

Asp His Leu Lys Glu Leu Gly Val Asn Cys Ile Glu Leu Met Pro Cys
305                 310                 315                 320

His Glu Phe Asn Glu Leu Glu Tyr Tyr Ser Tyr Asn Ser Val Leu Gly
                325                 330                 335

Asp Tyr Lys Phe Asn Phe Trp Gly Tyr Ser Thr Val Asn Phe Phe Ser
                340                 345                 350

Pro Met Gly Arg Tyr Ser Ser Ala Gly Leu Ser Asn Cys Gly Leu Gly
            355                 360                 365

Ala Ile Asn Glu Phe Lys Tyr Leu Val Lys Glu Ala His Lys Arg Gly
370                 375                 380

Ile Glu Val Ile Met Asp Val Val Phe Asn His Thr Ala Glu Gly Asn
385                 390                 395                 400

Glu Asn Gly Pro Ile Leu Ser Phe Arg Gly Ile Asp Asn Ser Val Phe
                405                 410                 415
```

```
Tyr Thr Leu Ala Pro Lys Gly Glu Phe Tyr Asn Tyr Ser Gly Cys Gly
            420                 425                 430

Asn Thr Phe Asn Cys Asn Asn Pro Ile Val Arg Gln Phe Ile Val Met
            435                 440                 445

Leu Arg Tyr Trp Val Thr Glu Met His Val His Gly Phe Arg Phe Asp
            450                 455                 460

Leu Ala Ser Ile Leu Thr Arg Ser Ser Ser Trp Asn Ala Val Asn
465                 470                 475                 480

Val Tyr Gly Asn Ser Ile Asp Gly Asp Val Ile Thr Thr Gly Thr Pro
                485                 490                 495

Leu Thr Ser Pro Pro Leu Ile Asp Met Ile Ser Asn Asp Pro Ile Leu
            500                 505                 510

Arg Gly Val Lys Leu Ile Ala Glu Ala Trp Asp Cys Gly Gly Leu Tyr
            515                 520                 525

Gln Val Gly Met Phe Pro His Trp Gly Ile Trp Ser Glu Trp Asn Gly
            530                 535                 540

Lys Tyr Arg Asp Met Val Arg Gln Phe Ile Lys Gly Thr Asp Gly Phe
545                 550                 555                 560

Ser Gly Ala Phe Ala Glu Cys Leu Cys Gly Ser Pro Asn Leu Tyr Gln
                565                 570                 575

Lys Gly Gly Arg Lys Pro Trp Asn Ser Ile Asn Phe Val Cys Ala His
            580                 585                 590

Asp Gly Phe Thr Leu Ala Asp Leu Val Thr Tyr Asn Asn Lys His Asn
            595                 600                 605

Leu Ala Asn Gly Glu Asp Asn Lys Asp Gly Glu Asn His Asn Asn Ser
610                 615                 620

Trp Asn Cys Gly Glu Glu Gly Glu Phe Ala Ser Ile Phe Val Lys Lys
625                 630                 635                 640

Leu Arg Lys Arg Gln Met Arg Asn Phe Phe Leu Cys Leu Met Val Ser
                645                 650                 655

Gln Gly Val Pro Met Ile Tyr Met Gly Asp Glu Tyr Gly His Thr Lys
                660                 665                 670

Gly Gly Asn Asn Asn Thr Tyr Cys His Asp Asn Tyr Ile Asn Tyr Phe
            675                 680                 685

Arg Trp Asp Lys Lys Asp Glu Ser Ser Ser Asp Phe Leu Arg Phe Cys
            690                 695                 700

Gly Leu Met Thr Lys Phe Arg His Glu Cys Glu Ser Leu Gly Leu Asp
705                 710                 715                 720

Gly Phe Pro Thr Ala Glu Arg Leu Gln Trp His Gly His Thr Pro Arg
                725                 730                 735

Thr Pro Asp Trp Ser Glu Thr Ser Arg Phe Val Ala Phe Thr Leu Val
            740                 745                 750

Asp Lys Val Lys Gly Glu Leu Tyr Ile Ala Phe Asn Ala Ser His Leu
            755                 760                 765

Pro Val Thr Ile Thr Leu Pro Asp Arg Pro Gly Tyr Arg Trp Gln Pro
770                 775                 780

Phe Val Asp Thr Gly Lys Pro Ala Pro Phe Asp Phe Leu Thr Asp Asp
785                 790                 795                 800

Val Pro Glu Arg Glu Thr Ala Ala Lys Gln Tyr Ser His Phe Leu Asp
                805                 810                 815

Ala Asn Gln Tyr Pro Met Leu Ser Tyr Ser Ser Ile Ile Leu Leu Leu
            820                 825                 830

Ser Ser Ala Asp Asp Ala
```

835

<210> SEQ ID NO 15
<211> LENGTH: 397
<212> TYPE: PRT
<213> ORGANISM: Solanum tuberosum

<400> SEQUENCE: 15

| Ser | Phe | Arg | Gly | Ile | Asp | Asn | Lys | Val | Tyr | Tyr | Met | Val | Asp | Leu | Asn |
|---|---|---|---|---|---|---|---|---|---|---|---|---|---|---|---|
| 1 | | | | 5 | | | | | 10 | | | | | 15 | |

| Asn | Asn | Ala | Gln | Leu | Leu | Asn | Phe | Ala | Gly | Cys | Gly | Asn | Thr | Phe | Asn |
| | | | 20 | | | | | 25 | | | | | 30 | | |

| Cys | Asn | His | Pro | Thr | Val | Met | Glu | Leu | Ile | Leu | Glu | Ser | Leu | Arg | His |
| | | 35 | | | | | 40 | | | | | 45 | | | |

| Trp | Val | Thr | Glu | Tyr | His | Val | Asp | Gly | Phe | Arg | Phe | Asp | Leu | Ala | Ser |
| | 50 | | | | | 55 | | | | | 60 | | | | |

| Val | Leu | Cys | Arg | Gly | Thr | Asp | Gly | Thr | Pro | Ile | Asn | Ala | Pro | Pro | Leu |
| 65 | | | | | 70 | | | | | 75 | | | | | 80 |

| Val | Lys | Ala | Ile | Ser | Lys | Asp | Ser | Val | Leu | Ser | Arg | Cys | Lys | Ile | Ile |
| | | | | 85 | | | | | 90 | | | | | 95 | |

| Ala | Glu | Pro | Trp | Asp | Cys | Gly | Gly | Leu | Tyr | Leu | Val | Gly | Lys | Phe | Pro |
| | | | 100 | | | | | 105 | | | | | 110 | | |

| Asn | Trp | Asp | Arg | Trp | Ala | Glu | Trp | Asn | Gly | Lys | Tyr | Arg | Asp | Asp | Ile |
| | | 115 | | | | | 120 | | | | | 125 | | | |

| Arg | Arg | Phe | Ile | Lys | Gly | Asp | Ala | Gly | Met | Lys | Gly | Asn | Phe | Ala | Thr |
| | 130 | | | | | 135 | | | | | 140 | | | | |

| Arg | Ile | Ala | Gly | Ser | Ala | Asp | Leu | Tyr | Arg | Val | Asn | Lys | Arg | Lys | Pro |
| 145 | | | | | 150 | | | | | 155 | | | | | 160 |

| Tyr | His | Ser | Val | Asn | Phe | Val | Ile | Ala | His | Asp | Gly | Phe | Thr | Leu | Tyr |
| | | | | 165 | | | | | 170 | | | | | 175 | |

| Asp | Leu | Val | Ser | Tyr | Asn | Asn | Lys | His | Asn | Asp | Ala | Asn | Gly | Glu | Gly |
| | | | 180 | | | | | 185 | | | | | 190 | | |

| Gly | Asn | Asp | Gly | Cys | Asn | Asp | Asn | Phe | Ser | Trp | Asn | Cys | Gly | Ile | Glu |
| | | 195 | | | | | 200 | | | | | 205 | | | |

| Gly | Glu | Thr | Ser | Asp | Ala | Asn | Ile | Asn | Ala | Leu | Arg | Ser | Arg | Gln | Met |
| | 210 | | | | | 215 | | | | | 220 | | | | |

| Lys | Asn | Phe | His | Leu | Ala | Leu | Met | Val | Ser | Gln | Gly | Thr | Pro | Met | Met |
| 225 | | | | | 230 | | | | | 235 | | | | | 240 |

| Leu | Met | Gly | Asp | Glu | Tyr | Gly | His | Thr | Arg | Tyr | Gly | Asn | Asn | Asn | Ser |
| | | | | 245 | | | | | 250 | | | | | 255 | |

| Tyr | Gly | His | Asp | Thr | Ala | Ile | Asn | Asn | Phe | Gln | Trp | Gly | Gln | Leu | Glu |
| | | | 260 | | | | | 265 | | | | | 270 | | |

| Ala | Arg | Lys | Asn | Asp | His | Phe | Arg | Phe | Phe | Ser | Lys | Met | Ile | Lys | Phe |
| | | 275 | | | | | 280 | | | | | 285 | | | |

| Arg | Leu | Ser | His | Asn | Val | Leu | Arg | Lys | Glu | Asn | Phe | Ile | Glu | Lys | Asn |
| | 290 | | | | | 295 | | | | | 300 | | | | |

| Asp | Ile | Thr | Trp | Leu | Glu | Asp | Asn | Trp | Tyr | Asn | Glu | Glu | Ser | Arg | Phe |
| 305 | | | | | 310 | | | | | 315 | | | | | 320 |

| Leu | Ala | Phe | Met | Leu | His | Asp | Gly | Asn | Gly | Asp | Ile | Tyr | Leu | Ala |
| | | | | 325 | | | | | 330 | | | | | 335 |

| Phe | Asn | Ala | His | His | Phe | Ser | Ile | Lys | Thr | Ala | Ile | Pro | Ser | Pro | Pro |
| | | | 340 | | | | | 345 | | | | | 350 | | |

| Arg | Asn | Arg | Ser | Trp | Tyr | Arg | Val | Val | Asp | Thr | Asn | Leu | Lys | Ser | Pro |
| | | 355 | | | | | 360 | | | | | 365 | | | |

```
Asp Asp Phe Val Ile Glu Gly Val Ser Gly Ile Ser Glu Thr Tyr Asp
    370                 375                 380

Val Ala Pro Tyr Ser Ala Ile Leu Leu Glu Ala Lys Gln
385                 390                 395

<210> SEQ ID NO 16
<211> LENGTH: 24
<212> TYPE: DNA
<213> ORGANISM: Artificial Sequence
<220> FEATURE:
<223> OTHER INFORMATION: Forward primer

<400> SEQUENCE: 16
gatcataact tgagttctaa gcgg                                            24

<210> SEQ ID NO 17
<211> LENGTH: 17
<212> TYPE: DNA
<213> ORGANISM: Artificial Sequence
<220> FEATURE:
<223> OTHER INFORMATION: Reverse primer

<400> SEQUENCE: 17
caggaaacag ctatgac                                                    17

<210> SEQ ID NO 18
<211> LENGTH: 13
<212> TYPE: PRT
<213> ORGANISM: Solanum tuberosum

<400> SEQUENCE: 18

Glu Tyr Val Ile His Gln Val Leu Tyr Leu Thr Leu Leu
  1               5                  10

<210> SEQ ID NO 19
<211> LENGTH: 883
<212> TYPE: PRT
<213> ORGANISM: Solanum tuberosum
<220> FEATURE:
<221> NAME/KEY: SITE
<222> LOCATION: (603, 606)
<223> OTHER INFORMATION: Xaa = unknown amino acid

<400> SEQUENCE: 19

His Cys Val Leu Leu Met Ala Thr Ser Pro Ile Gln Leu Ala Val His
  1               5                  10                  15

Ser Arg Leu Leu Ser Tyr Gly Ser Thr Glu Ser Thr Lys Leu Val Pro
             20                  25                  30

Ser Ser Ser Gly Asn Arg Gly Lys Ile Val Cys Ser Leu Arg Lys Leu
         35                  40                  45

Glu Leu Glu Asp Met Asn Phe Ser Gly Ile Gly Arg Asn Asn Asp Gln
     50                  55                  60

Glu Ala Pro Arg Arg Ala His Arg Arg Lys Ala Leu Ser Ala Ser Arg
 65                  70                  75                  80

Ile Ser Leu Val Pro Ser Ala Lys Arg Val Pro Thr Tyr Leu Phe Arg
                 85                  90                  95

Thr Asp Ile Gly Gly Gln Val Leu Val Leu Val Glu Lys Thr Asn Gly
            100                 105                 110

Lys Tyr Lys Val Leu Val Glu Val Leu Pro Leu Glu Leu Ser Asp Ala
        115                 120                 125

His Ser Glu Leu Val Met Val Trp Gly Leu Phe Arg Ser Asp Ala Leu
    130                 135                 140
```

-continued

```
Cys Phe Met Pro Leu Asp Leu Asn Arg Arg Gly Ala Asp Gly Lys Ser
145                 150                 155                 160

Ser Thr Val Glu Thr Pro Phe Val Gln Gly Pro Ser Gly Lys Val Thr
                165                 170                 175

Val Glu Leu Asp Phe Glu Ala Ser Leu Ala Pro Phe Tyr Ile Ser Phe
            180                 185                 190

Tyr Met Lys Ser Gln Leu Val Ser Asp Met Glu Asn Ser Glu Ile Arg
        195                 200                 205

Ser His Arg Asn Thr Asn Phe Val Val Pro Val Gly Leu Ser Ser Gly
    210                 215                 220

His Pro Ala Pro Leu Gly Ile Ser Phe Gln Pro Asp Gly Ser Val Asn
225                 230                 235                 240

Phe Ala Leu Phe Ser Arg Ser Ala Arg Ser Val Val Leu Cys Leu Tyr
                245                 250                 255

Asp Asp Ile Ser Val Glu Lys Pro Ser Leu Glu Ile Asp Leu Asp Pro
            260                 265                 270

Tyr Ile Asn Arg Ser Gly Asp Ile Trp His Ala Leu Asp Cys Ser
        275                 280                 285

Leu Pro Phe Lys Thr Tyr Gly Tyr Arg Cys Lys Ala Thr Thr Ser Gly
    290                 295                 300

Lys Gly Glu Leu Val Leu Leu Asp Pro Tyr Ala Lys Val Ile Arg Arg
305                 310                 315                 320

Val Ile Pro Arg Gln Gly Gly Ser Glu Ile Arg Pro Lys Tyr Leu Gly
                325                 330                 335

Glu Leu Cys Leu Glu Pro Gly Tyr Asp Trp Ser Gly Asp Val Pro Pro
            340                 345                 350

Ser Leu Pro Met Glu Lys Leu Ile Ile Tyr Arg Leu Asn Val Thr Gln
        355                 360                 365

Phe Thr Lys Asp Lys Ser Ser Lys Leu Pro Asp Asp Leu Ala Gly Thr
    370                 375                 380

Phe Ser Gly Ile Ser Glu Lys Trp His His Phe Lys Asp Leu Gly Val
385                 390                 395                 400

Asn Ala Met Leu Leu Glu Pro Ile Phe Pro Phe Asp Glu Gln Lys Gly
                405                 410                 415

Pro Tyr Phe Pro Trp His Phe Ser Pro Gly Asn Met Tyr Gly Pro
            420                 425                 430

Ser Gly Asp Pro Leu Ser Ala Ile Lys Ser Met Lys Asp Met Val Lys
        435                 440                 445

Lys Leu His Ala Asn Gly Ile Glu Val Phe Leu Glu Val Val Phe Thr
    450                 455                 460

His Thr Ala Glu Asp Ala Pro Leu Met Asn Val Asp Asn Phe Ser Tyr
465                 470                 475                 480

Cys Ile Lys Gly Gly Gln Tyr Leu Asn Ile Gln Asn Ala Leu Asn Cys
                485                 490                 495

Asn Tyr Pro Ile Val Gln Gln Met Ile Leu Asp Cys Leu Arg His Trp
            500                 505                 510

Val Ile Glu Phe His Ile Asp Gly Phe Val Phe Val Asn Ala Ser Ser
        515                 520                 525

Leu Leu Arg Gly Phe Asn Gly Glu Ile Leu Ser Arg Pro Pro Leu Val
    530                 535                 540

Glu Ala Ile Ala Phe Asp Pro Ile Leu Ser Lys Val Lys Met Ile Ala
545                 550                 555                 560
```

```
Asp Asn Trp Asn Pro Leu Thr Asn Asp Ser Lys Glu Asn Leu Phe Pro
            565                 570                 575

His Trp Arg Arg Trp Ala Glu Ile Asn Met Arg Phe Cys Asp Asp Ile
        580                 585                 590

Arg Asp Phe Leu Arg Gly Glu Gly Leu Leu Xaa Asn Leu Xaa Thr Arg
    595                 600                 605

Leu Cys Gly Ser Gly Asp Ile Phe Ala Gly Arg Gly Pro Ala Phe
610                 615                 620

Ser Phe Asn Tyr Ile Ala Arg Asn Ser Gly Leu Thr Leu Val Asp Leu
625                 630                 635                 640

Val Ser Phe Ser Ser Asn Glu Val Ala Ser Glu Leu Ser Trp Asn Cys
            645                 650                 655

Gly Gln Glu Gly Ala Thr Thr Asn Asn Ile Val Leu Glu Arg Arg Leu
        660                 665                 670

Lys Gln Val Arg Asn Phe Leu Phe Ile Leu Phe Ile Ser Leu Gly Val
    675                 680                 685

Pro Val Leu Asn Met Gly Asp Glu Cys Gly Gln Ser Ser Gly Gly Pro
690                 695                 700

Pro Ala Tyr Asp Ala Arg Lys Ser Leu Gly Trp Asn Thr Leu Lys Thr
705                 710                 715                 720

Gly Phe Gly Thr Gln Ile Ala Gln Phe Ile Ser Phe Leu Ser Asn Leu
            725                 730                 735

Arg Met Arg Arg Ser Asp Leu Leu Gln Lys Arg Thr Phe Leu Lys Glu
        740                 745                 750

Glu Asn Ile Gln Trp His Gly Ser Asp Gln Ser Pro Pro Lys Trp Asp
    755                 760                 765

Gly Pro Ser Ser Lys Phe Leu Ala Met Thr Leu Lys Ala Asp Ala Glu
770                 775                 780

Val Ser Gln Thr Leu Val Ser Asp Ile Val Gly Asp Leu Phe Val Ala
785                 790                 795                 800

Phe Asn Gly Ala Gly Asp Ser Glu Ile Val Ile Leu Pro Pro Pro
            805                 810                 815

Thr Asp Met Val Trp His Arg Leu Val Asp Thr Ala Leu Pro Phe Pro
        820                 825                 830

Gly Phe Phe Asp Glu Lys Gly Thr Pro Val Glu Asp Leu Val Ala
    835                 840                 845

Tyr Glu Met Lys Ser His Ser Cys Leu Leu Phe Glu Ala Gln Arg Leu
850                 855                 860

Ala Glu Ile Asp Ser Ser Lys Arg Lys Gln Ile Arg Leu Ser Ser
865                 870                 875                 880

Lys Arg Gln

<210> SEQ ID NO 20
<211> LENGTH: 20
<212> TYPE: PRT
<213> ORGANISM: Solanum tuberosum

<400> SEQUENCE: 20

Phe Val Lys Pro Leu Ser Ile Tyr Ile Cys Leu Asn Lys Arg Leu Phe
  1               5                  10                  15

Phe Leu Asn Lys
            20

<210> SEQ ID NO 21
<211> LENGTH: 9
```

```
<212> TYPE: PRT
<213> ORGANISM: Solanum tuberosum

<400> SEQUENCE: 21

Glu Asp Phe Thr Glu Asn Thr Cys Ile
  1               5

<210> SEQ ID NO 22
<211> LENGTH: 12
<212> TYPE: PRT
<213> ORGANISM: Solanum tuberosum

<400> SEQUENCE: 22

Thr Phe Ser Phe Ala Ala Ser Asn Lys Lys Lys Lys
  1               5                  10

<210> SEQ ID NO 23
<211> LENGTH: 5
<212> TYPE: PRT
<213> ORGANISM: Solanum tuberosum

<400> SEQUENCE: 23

Phe His Ser Pro Ser
  1               5

<210> SEQ ID NO 24
<211> LENGTH: 42
<212> TYPE: PRT
<213> ORGANISM: Solanum tuberosum

<400> SEQUENCE: 24

Val Glu Val Asn Gln Leu Gln Ile Leu Leu Tyr Ala Val Arg Cys Tyr
  1               5                  10                  15

Phe Val Asn Lys Ser Lys Lys Gln Asp Arg Thr Glu Leu Gln Thr Asp
             20                  25                  30

Lys Ile Cys Glu Glu Glu Ala Asp Asp Leu
         35                  40

<210> SEQ ID NO 25
<211> LENGTH: 10
<212> TYPE: PRT
<213> ORGANISM: Solanum tuberosum

<400> SEQUENCE: 25

Asp Thr Pro Cys Ile Leu Ile Ala Phe Ile
  1               5                  10

<210> SEQ ID NO 26
<211> LENGTH: 36
<212> TYPE: PRT
<213> ORGANISM: Solanum tuberosum
<220> FEATURE:
<221> NAME/KEY: SITE
<222> LOCATION: (4, 34)
<223> OTHER INFORMATION: Xaa = unknown amino acid

<400> SEQUENCE: 26

Asn Lys Ile Xaa Val Lys Leu Ser Val Arg Lys Lys Lys Lys Lys Lys
  1               5                  10                  15

Ile Lys Lys Lys Lys Lys Lys Lys Pro Trp Tyr Pro Asp Pro Arg
             20                  25                  30

Ile Xaa Tyr Gln
         35
```

```
<210> SEQ ID NO 27
<211> LENGTH: 31
<212> TYPE: PRT
<213> ORGANISM: Solanum tuberosum

<400> SEQUENCE: 27

Leu Pro Gly Leu Cys Cys Phe Arg Cys Cys Pro Cys Val Ile Thr Val
 1               5                  10                  15

Leu Pro Pro Ser Gly Leu Asp Ser Ser Asn Trp Asn Ser Gly Cys
             20                  25                  30

<210> SEQ ID NO 28
<211> LENGTH: 6
<212> TYPE: PRT
<213> ORGANISM: Solanum tuberosum

<400> SEQUENCE: 28

Pro Ile Asp Val Val Cys
 1               5

<210> SEQ ID NO 29
<211> LENGTH: 5
<212> TYPE: PRT
<213> ORGANISM: Solanum tuberosum

<400> SEQUENCE: 29

Ala Glu Ile Leu Gln
 1               5

<210> SEQ ID NO 30
<211> LENGTH: 19
<212> TYPE: PRT
<213> ORGANISM: Solanum tuberosum

<400> SEQUENCE: 30

Ala Thr Ser Phe Val Gln Lys Lys Lys Lys Lys Lys Lys Lys Lys
 1               5                  10                  15

Lys Lys Lys
```

STARCH DEBRANCHING ENZYMES

This application is a 371 of PCT/GB98/02280 filed Jul. 30, 1998.

TECHNICAL FIELD

The present invention relates to enzymes having starch debranching activity. It further relates to nucleic acid encoding such enzymes, and methods of producing and using such enzymes and nucleic acid.

PRIOR ART

Starch is composed of highly branched (amylopectin), and lightly branched (amylose) glucan polymers arranged in a three-dimensional, semicrystalline structure, the starch granule. The degree of branching of amylopectin and the spatial organization of branches within the starch granule are very important in determining the physical properties of the starch and hence its value as a raw material for industry. The traditional view is that the branching pattern of amylopectin, and hence the way in which it is organised to form a granule, is determined by starch-branching enzymes which cleave short glucans from the non-reducing ends of chains and join them to residues within the same or an adjacent chain via α(1–6) linkages to form branches. There is, however, increasing evidence that the branching pattern of amylopectin results from the combined actions of branching and debranching enzymes.

"Debranching enzymes" hydrolyse α(1–6) glucosidic linkages in glucans. In plants, two quite different types have been described:

The "cullulanase" (EC 3.2.1.41) type is widely distributed in starch-degrading organs and in the chloroplasts of leaves. It is capable of the hydrolysis of the α(1–6) linkages of pullulan, amylopectin and α-limit dextrins, but usually cannot hydrolyse glycogen.

The second type of debranching enzyme, the "isoamylase" (EC 3.2.1.68) type, has been described only in potato tubers and maize endosperm, but this is probably because there is, at the moment, no specific assay for isoamylase activity in crude extracts (i.e. where other hydrolysing enzymes may be present). It can hydrolyse the α(1–6) linkages of amylopectin, glycogen and α-limit dextrins, but not pullulan.

Evidence that debranching enzymes may be involved in determining amylopectin structure comes from analysis of the sugary (su 1) mutant of maize (Pan and Nelson 1984, James et al. 1995), the sugary mutant of rice (Nakamura et al. 1996a) and the STA 7 mutant of Chlamydomonas (Mouille et al. 1996). All three mutations reduce or eliminate synthesis of conventional starch and cause the accumulation of a highly-branched, water-soluble glucan known as phytoglycogen. This change is accompanied by a reduction in the activity of debranching enzymes. In both maize and rice endosperm the activity of the pullulanase type of debranching enzyme is decreased, and in Chlamydomonas the activity of a debranching enzyme of unknown type disappears. In general terms, therefore, these phenotypes suggest that debranching enzyme is involved in determining the structure of amylopectin. However, understanding of the mutant phenotypes is far from complete.

Before the priority date of the present application, the sul locus from maize had been shown to encode a polypeptide which is very similar in amino-acid sequence to the bacterial isoamylase type of debranching enzyme, and not to pullulanases (James et al. 1995). Note, though, that the 5' end of the sequence was not necessarily complete in this publication. No effect of the mutation on isoamylase activity in the endosperm was reported. The way in which the mutation brings about a decrease in pullulanase activity, and the relationship between this decrease and the accumulation of phytoglycogen were also not known.

After the priority date of the present application, nearly full-length maize SU1 was expressed in E. coli and purified. The recombinant enzyme was classified as an isoamylase (Rahman et al, 1998 Plant Physiol 117: 425–435).

Neither the rice nor the Chlamydomonas mutations have been fully characterised. In the former case, it has been established that the gene at the sugary locus does not encode the pullulanase that decreases in activity in the mutant endosperm (Nakamura et al. 1996b). In the latter case, the nature of the gene at the STA7 locus is not known.

The general effects of these mutations form the basis for a new model to explain the synthesis of amylopectin and its organisation to form a granule (Ball et al. 1996). Briefly, it is proposed that debranching enzyme acts to "trim" a highly-branched phytoglycogen-like structure synthesised at the periphery of the growing granule. This creates the branching pattern typical of amylopectin which, unlike the branching pattern of phytoglycogen, allows the polymer to pack in an organised manner to form the semi-crystalline matrix of the granule.

A critical assessment of the validity of this model is not yet possible, in part because of the lack of understanding of the mutations on which it is based, and in part because of the lack of information about debranching enzymes generally, and in starch-synthesising organs in particular. The nature, number and intracellular location of proteins with debranching activity is not known for any starch-synthesising organ, and sequences have been reported for only one plant isoamylase (the sul gene product) and a very few pullulanases. It is not known whether either isoamylase or pullulanase actually have the properties and specificities required by the Ball model.

Regardless of the validity of the Ball model, it seems highly likely that debranching enzymes play an important role in determining amylopectin structure, and hence in determining the physical properties of starch. The fact that the sul gene encodes an isoamylase suggests that this type of enzyme in particular may be involved. The decrease in pullulanase activity in the sul and sugary mutants also implicates this type of enzyme, and it has been reported (J. Kossmann and colleagues, MPI-MPP, Golm, Germany; verbal reports at open meetings) that modification of pullulanase activity in potato tubers brings about changes in the physical properties of the tuber starch.

Patent application WO 95/04826 [Kossmann et al] relates to a debranching enzyme obtained from potato. From the purification procedure used to obtain the amino acid sequence information it would appear that this relates to a single enzyme of the pullulanase type.

Patent application WO 95/03513 [Barry et al] relates to an isoamylase obtained from flavobacterium spp. The application does not disclose any corresponding enzymes or sequences from plants.

It can thus be seen that novel starch debranching enzymes, particularly those from plants, and particularly isoamylases, may provide a useful contribution to the art.

SUMMARY OF THE INVENTION

In a first aspect of the invention there is disclosed an isolated nucleic acid which comprises a nucleotide sequence which encodes a polypeptide which has the properties of an isoamylase, and is obtainable from *Solanum tuberosum*.

Preferably the nucleic acid molecule has the sequence shown in any of Seq ID Nos 1 to 3 or is degeneratively equivalent or complementary thereto.

Seq ID Nos 1 to 3 (FIGS. 1 to 3) represent nucleotide sequences derived by the present inventors from cDNA clones (designated 21, 15 and 9 respectively) from potato tubers and minitubers. Clone 15 came from a minituber library; clone 9 from a tuber library and clone 21 was found in both types of library. Each of these clones encodes all or part of an independent novel starch debranching enzyme.

The amino acid sequences for clones 21, 15 and 9 are given as Seq ID Nos 4–6 (FIGS. 4–6) respectively The original nucleotide sequences for clones 21, 15 and 9 which were determined initially by the inventors are given as Seq ID Nos 10–12 (FIGS. 10–12) respectively. Owing to very minor variations in the sequencing process these differ at a very few positions from the sequences above: however in the case of clones 21 and 15 there is in excess of 99.5% identity between new and old sequences. Clone 9 has also been extended at its 3' terminus (still in excess of 99% identity). Corresponding amino acid sequences are at Seq ID Nos 13–15 (FIGS. 13–15) respectively.

TABLE 1

|  | Similarity | Identity |
|---|---|---|
| sul |  |  |
| C9 | 63 | 46 |
| C15 | 82 | 71 |
| C21 | 58 | 35 |
| Isopsean |  |  |
| C9 | 53 | 32 |
| C15 | 54 | 31 |
| C21 | 48 | 23 |
| Klepn |  |  |
| C9 | 46.5 | 21.6 |
| C15 | 48.5 | 23.2 |
| C21 | 50.7 | 22.3 |
| Kleae |  |  |
| C9 | 47.3 | 21.6 |
| C15 | 45.6 | 21.9 |
| C21 | 49.1 | 21.8 |
| Sopulspo |  |  |
| C9 | 49.4 | 26.8 |
| C15 | 43.6 | 22.1 |
| C21 | 46.6 | 21.8 |
| Puli |  |  |
| C9 | 49.1 | 27.3 |
| C15 | 50 | 26.6 |
| C21 | 49.1 | 22.6 |

All of these sequences are unique, but show significant similarity at the level of predicted amino-acid sequence to the su1 gene product of maize and the isoamylases of micro-organisms.

A comparison of the clones was made with isoamylases (Table 1—above); namely the su1 gene (Sulzmay—EMBL Ac No U18908) and Isopseam (EMBL Ac No J03871; M28370) which is bacterial. Also with Pula_klepn (EMBL Ac No X52181; M32702) and Pula_kleae (EMBL Ac No M16187) which are bacterial pullulanases. Plus Sopulspo (EMBL Ac No X83969) which is a pullulanase from spinach.

Conserved domains I to IV occur in the amino acid sequences of clones 21, 15 and 9 at the following positions (Table 2):

TABLE 2

|  | Domain | | | |
|---|---|---|---|---|
|  | I | II | III | IV |
| C9 | 352–357 | 426–434 | 467–470 | 535–540 |
| C15 | 344–349 | 415–423 | 475–478 | 543–548 |
| C21 | 455–460 | 515–523 | 556–559 | 623–628 |

This domain structure is typical of isoamylases; domain III does not occur in pullulanases.

The relationship between the various sequences is best illustrated by means of the dendogram (FIG. 9) which shows the debranching enzymes in 2 groups, with clones 15, 9 and 21 all aligning with the isoamylases. Clone 15 is most similar to the Su1 gene.

Since the clones show greater similarity to the isoamylase sequences, they have been putatively identified as isoamylases, and they are described as such hereinafter; however it will be understood by the skilled person that the essence of the present invention is the making available of novel starch debranching enzymes, for instance for some of the purposes listed below, and this contribution to the art would not be diminished should the enzymes have properties not wholly consistent with the isoamylases described in the prior art. Indeed different properties and/or specificities may be advantageous for certain applications.

Thus the present inventors have for the first time demonstrated the existence of multiple forms of isoamylase in the potato tuber.

The nucleic acid molecules or vectors (see below) according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may include cDNA, RNA, genomic DNA and may be wholly or partially synthetic. "Nucleic acid" and "nucleic acid molecule" have the same meaning.

The term "isolate" encompasses all these possibilities. Where a DNA sequence is specified, e.g. with reference to a figure, unless context requires otherwise the RNA equivalent, with U substituted for T where it occurs, is encompassed.

Thus nucleic acid according to the present invention may comprise the sequence or complement of any one of Seq ID Nos. 1 to 3, including coding and/or non-coding regions where appropriate.

The disclosure of these sequences opens up for the first time the ability to manipulate the starch debranching activity in plants in a number of important respects. These include, inter alia, the ability to:

a) Reduce the activity of each of the isoamylases in potato tuber and other plants in which homologous enzymes are expressed.

b) Increase debranching enzyme activity in the potato tuber, by high level expression of one or more of each of the complete or partial potato cDNAs or sequences based thereon.

c) Alter the activity of each of the isoamylases in various different subcellular compartments (e.g. plastids or cytosol) or at various different developmental stages.

d) Study the effect of transformation experiments on the activities of isoforms of the debranching enzymes and related enzymes of starch synthesis and degradation, on the rates of starch synthesis, on starch structure, on the accumulation of soluble carbohydrates, and on the degradation of starch during sprouting.

e) Produce novel starch types in transgenic lines.

f) Produce novel isoamylases having modified activity.

g) Isolate corresponding isoamylases.

In essence the various nucleic acid molecules of the present invention may ultimately be used to promote or alter (in respect of the reaction catalysed) the nature of the starch debranching activity in a particular cell or organism. In some embodiments they may be used to repress starch debranching activity compared with that expressed in the untransformed cell or organism e.g. delay, retard, inhibit or slow down such activity.

In particular, alteration of debranching enzyme activity starch-synthesising cells would modify the structure of the starch accumulated in those cells in novel ways. The modifications to the starch which may be achieved using the nucleic acid molecules of the present invention include:

1. Decrease the degree of branching of amylopectin thereby creating a starch that may swell less or form a stronger gel on heating in water. This may be achieved by increasing the activity of starch debranching enzymes, preferably through the over-expression of one, and most preferably more than one, endogenous or exogenous debranching enzymes.

2. Increase the degree of branching of starch thereby opening up the possibility of increasing its swelling properties and its ability to form a paste rather than a gel when heated in water. Particularly embraced is the production of phytoglycogen instead of some or all of the normal starch. This may be achieved by decreasing activity through the expression of antisense RNA.

3. Changing the branching pattern of amylopectin in other ways, thereby altering the physical properties of the starch. This may be accomplished by changing the isoform composition of debranching enzymes in a given tissue. Thus it may be achieved by selective decreases or increases in activity or subcellular localisation of endogenous isoamylases or the introduction of novel isoamylases and/or mutants, variants, derivatives or alleles thereof.

These and other aspects of the present invention will now be described in more detail.

Thus in a second aspect of the present invention there is disclosed a nucleic acid molecule encoding a mutant, variant, derivative or allele of a molecule of the first aspect, preferably to Seq ID Nos 1 to 3. Preferred mutants, variants, derivatives and alleles are those which are homologous to the respective Seq ID No and which also encode a product which has the ability to promote starch debranching activity. Mutants, variants or derivatives of the complement of Seq ID Nos 1 to 3 are those which have the ability to repress starch debranching activity.

Methods for producing or identifying such a mutant, variant, derivative or allele (or other homologue) and assessing homology and function will now be discussed.

Changes to a sequence, to produce a mutant, variant or derivative, may be by way of one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence (i.e. 'degeneratively equivalent') are included.

As is well-understood, homology at the amino acid level (i.e the encoded product of the nucleic acid molecule when expressed properly in frame) is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art, or, and this may be preferred, the standard program BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation. Indeed, such changes may confer slightly advantageous properties on the peptide.

Also included are nucleic acids having a few "non-conservative" substitutions. As is well known to those skilled in the art, substitutions to regions of a peptide which are not critical in determining its conformation may not greatly affect its activity because they do not greatly alter the peptide's three dimensional structure. Those in important regions (e.g. conserved regions I to IV) may confer advantageous properties on the polypeptide product. Similarly it may be desirable to alter or otherwise manipulate the transit peptide sequence e.g. in clones 21 and 15, in order to alter the targeting or localisation properties of the enzymes.

A mutant, variant or derivative amino acid sequence in accordance with the present invention may include within the amino acid sequence encoded by Seq ID Nos 1 to 3 (see FIGS. 4 to 6) a single amino acid change with respect to the sequence shown or 2, 3, 4, 5, 6, 7, 8, or 9 changes, about 10, 15, 20, 30, 40 or 50 changes, or greater than about 50, 60, 70, 80 or 90 changes.

In addition to one or more changes within the coding sequences of any one of Seq ID Nos 1 to 3, a mutant, variant or derivative nucleic acid molecule may have additional nucleotides at the 5' or 3' terminii. In particular it may be desirable to have a full length clone e.g. including any coding or non-coding regions (e.g. promoter) not included in the sequences but present in nature. These regions can be identified using methods analogous to those used to clone homologues or alleles as set out below.

In a third aspect of the present invention there is provided a method of identifying, mapping and/or cloning homologues or alleles from a plant species (including potato) which method employs all or part of the nucleotide sequence of Seq ID Nos 1 to 3. Suitable methods based on the sequences provided by the present invention are discussed below. If a portion of this a sequence is used this will be of sufficient length to identify homologues or alleles as described below.

Optionally, if a portion of nucleotide sequence is used, then this portion will not itself be identical to any part of Seq ID No 7 (FIG. 7) which was used to detect clones 21, 15 and 9. Such a probe may therefore detect homologues and/or alleles which would not be detected using that Seq ID No 7.

In one embodiment of the third aspect, the nucleotide sequence of any one of Seq ID Nos 1 to 3, or any part thereof, may be used in a data-base search to find homologous sequences, expression products of which can be tested for ability to influence starch debranching, particularly for isoamylase activity. This may be achieved, for instance, using the vectors of the present invention discussed hereinafter.

In a further embodiment of the third aspect, an isoamylase allele or homologue in accordance with the present invention is also obtainable by means of a method which includes providing a preparation of nucleic acid, e.g. from cells from a starch accumulating organ or tissue of a plant, providing a nucleic acid molecule having a nucleotide sequence shown in or complementary to a nucleotide sequence shown in any one of Seq ID Nos 1 to 3, preferably from within the coding sequence, contacting nucleic acid in said preparation with said nucleic acid molecule under conditions for hybridisation of said nucleic acid molecule to any said gene or homologue in said preparation, and identifying said gene or homologue if present by its hybridisation with said nucleic acid molecule.

Thus probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Test nucleic acid may be provided from a cell as genomic DNA, cDNA or RNA, or a mixture of any of these, preferably as a library in a suitable vector. The information derived using genomic DNA may also be used in mapping, and in identifying associated non-expressed elements e.g. promoters.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR (see below), RN'ase cleavage and allele specific oligonucleotide probing.

Preliminary experiments may be performed by hybridising under low stringency conditions. For probing, preferred conditions are those which are stringent enough for there to be a simple pattern with a small number of hybridisations identified as positive which can be investigated further. It is well known in the art to increase stringency of hybridisation gradually until only a few positive clones remain. Suitable conditions would be achieved when a large number of hybridising fragments were obtained while the background hybridisation was low. Using these conditions nucleic acid libraries, e.g. cDNA libraries representative of expressed sequences, may be searched.

Those skilled in the art are well able to employ suitable conditions of the desired stringency for selective hybridisation, taking into account factors such as oligonucleotide length and base composition, temperature and so on. For instance, screening may initially be carried out under conditions, which comprise a temperature of about 37° C. or less, a formamide concentration of less than about 50%, and a moderate to low salt (e.g. Standard Saline Citrate ('SSC')= 0.15 M sodium chloride; 0.15 M sodium citrate; pH 7) concentration.

Alternatively, a temperature of about 50° C. or less and a high salt (e.g. 'SSPE'=0.180 mM sodium chloride; 9 mM disodium hydrogen phosphase; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid.

Suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

Hybridisation is generally followed by identification of successful hybrids and then isolation of nucleic acid which has hybridised, which may involve one or more steps of PCR (see below).

Thus one part of the present invention is a probe for use in this method.

In a further embodiment of this aspect of the present invention, hybridisation of a nucleic acid molecule to an allele or homologue may be determined or identified indirectly, e.g using a nucleic acid amplification reaction, particularly the polymerase chain reaction (PCR). PCR requires the use of two primers to specifically amplify target nucleic acid, so preferably two nucleic acid molecules with sequences characteristic of any one of Seq ID Nos 1 to 3 are employed. However, if RACE is used (see below) only one such specific primer may be needed. Characteristic in this sense is preferably in the sense of distinguishing them from known probes or sequences e.g. those associated with the Su1 gene.

PCR techniques for the amplification of nucleic acid are described in U.S. Pat. No. 4,683,195 and Saiki et al. *Science* 239: 487–491 (1988). PCR includes steps of denaturation of template nucleic acid (if double-stranded), annealing of primer to target, and polymerisation. The nucleic acid probed or used as template in the amplification reaction may be genomic DNA, cDNA or RNA. PCR may be used to amplify specific sequences from genomic DNA, specific RNA sequences and cDNA transcribed from mRNA. References for the general use of PCR techniques include Mullis et al, Cold Spring Harbor Symp. Quant. Biol., 51:263, (1987), Ehrlich (ed), PCR technology, Stockton Press, NY, 1989, Ehrlich et al, Science, 252:1643–1650, (1991), "PCR protocols; A Guide to Methods and Applications", Eds. Innis et al, Academic Press, New York, (1990).

Prior to any PCR that is to be performed, the complexity of a nucleic acid sample may be reduced where appropriate by creating a cDNA library for example using RT-PCR or by using the phenol emulsion reassociation technique (Clarke et al. (1992) NAR 20, 1289–1292) on a genomic library.

Thus a method involving use of PCR in obtaining nucleic acid according to the present invention may include providing a preparation of plant nucleic acid, providing a pair of nucleic acid molecule primers useful in (i.e. suitable for) PCR, at least one of said primers having a sequence shown in or complementary to all or part of a sequence shown in any one of Seq ID NOs 1 to 3, contacting nucleic acid in said preparation with said primers under conditions for performance of PCR, performing PCR and determining the presence or absence of an amplified PCR product. The presence of an amplified PCR product may indicate identification of a gene of interest or fragment thereof.

Thus the methods of the invention may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolated hybridised nucleic acid.

The primers for use in these methods form one part of the present invention.

In any case, an oligonucleotide for use in probing or nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length. For optimum specificity, primers of 16–24 nucleotides in length may be preferred. Those skilled in the art are well versed in the design of primers for use processes such as PCR.

In all cases the nucleic acids of the second aspect, or identified using the third aspect, share homology with those of the first aspect. Homology may be at the nucleotide sequence and/or amino acid sequence level. Preferably, there is at least about 83% homology, most preferably at least about 85%, 90%, 95%, 96%, 97%, 98%, 99% or 99.5% homology.

Homology may be over the full-length of the relevant sequence shown herein, or may more preferably be over a contiguous sequence of about or greater than about 20, 25, 30, 33, 40, 50, 67, 133 or more amino acids or codons, compared with the relevant amino acid sequence or nucleotide sequence as the case may be.

Similarly the mutant, variant, derivative or allele (or other homologue) in accordance with the present invention will promote, alter or repress the starch debranching activity of a cell into which it is introduced.

One possible mode of analysis of this activity is by transformation to assess function on introduction into a plant, plant cell or other cell of interest; methodology for such transformation is described in more detail below.

The nucleic acid of the present invention, which may contain for example DNA corresponding to any one of Seq ID Nos 1 to 3, may be in the form of a recombinant and preferably replicable vector.

Such vectors form a fourth aspect of the present invention.

DNA vector is defined to include, inter alia, any plasmid, cosmid, phage or Agrobacterium binary vector in double or single stranded linear or circular form which may or may not be self transmissible or mobilizable. Can transform prokaryotic or eukaryotic host either by integration into the cellular genome or exist extrachromosomally (e.g. autonomous replicating plasmid with an origin of replication). Vectors may be introduced into hosts by any appropriate method e.g. conjugation, mobilisation, transformation, transfection, transduction or electoporation. Also included are shuttle vectors by which is meant a DNA vehicle capable, naturally or by design, of replication in both the actinomycetes and related species and in bacteria and/or eucaryotic (e.g. higher plant, mammalian, yeast or fungal cells).

A vector including nucleic acid according to the present invention need not include a promoter or other regulatory sequence, particularly if the vector is to be used to introduce the nucleic acid into cells for recombination into the genome.

However, in a preferred embodiment of the fourth aspect the vector is an expression vector. Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology,* Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711–8721 (1984)) and Guerineau and Mullineaux (1993) (Plant transformation and expression vectors. In: Plant Molecular Biology Labfax (Croy RRD ed) Oxford, BIOS Scientific Publishers, pp 121–148).

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Thus nucleic acid molecules of the present invention may be under the control of an appropriate promoter or other regulatory elements for expression in a host cell such as a microbial, e.g. bacterial, or plant cell. In the case of genomic DNA, this may contain its own promoter or other regulatory elements and in the case of cDNA this may be under the control of an appropriate promoter or other regulatory elements for expression in the host cell.

Thus one aspect the present invention provides a gene construct, preferably a replicable vector, comprising a promoter operatively linked to a nucleotide sequence provided by the present invention, e.g. any one of Seq ID Nos 1 to 3, the complement, or any mutant, variant or allele thereof.

By "promoter" is meant a sequence of nucleotides from which transcription may be initiated of DNA operably linked downstream (i.e. generally in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

The promoter may include one or more sequence motifs or elements conferring developmental and/or tissue-specific regulatory control of expression. Other regulatory sequences may be included, for instance as identified by mutation or digest assay in an appropriate expression system or by sequence comparison with available information, e.g. using a computer to search on-line databases. Sequences for intra- or intercellular targetting may also be included e.g. plastid targetting sequences as described in, or modified from, Stark et al (1992) Science 258: 287–292. Also included may be appropriate untranscribed regions e.g. which cause the addition of the polyadenylate nucleotides to 3' end of transcribed RNA.

Suitable promoters may include the Cauliflower Mosaic Virus 35S (CaMV 35S) gene promoter that is expressed at a high level in virtually all plant tissues (Benfey et al, 1990a and 1990b). Other promoters may include the tuber specific B33 promoter (Rocha-Sosa et al (1989) EMBO J 8:23–29), or the patatin (class I) promoter.

In one embodiment of the fourth aspect these is disclosed a gene construct, preferably a replicable vector, comprising an inducible promoter operatively linked to a nucleotide sequence provided by the present invention.

The present invention also provides plants transformed with said gene construct and methods comprising introduction of such a construct into a plant cell and/or induction of expression of a construct within a plant cell, by application of a suitable stimulus, an effective exogenous inducer.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

A suitable inducible promoter is the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

The vectors of the fourth aspect of the invention may be used, inter alia, to transform plants and plant cells thereby altering their properties in a number of important respects.

Thus specific changes in activity of individual forms of isoamylase may be brought about by sense or antisense transformation. The disclosure by the present inventors of several forms of isoamylase has opened up the possibility of 'fine tuning' their effect(s) on amylopectin structure and hence on the properties of starch, depending upon which isoform is changed, the degree to which the activity is increased or decreased, and the timing of this change in relation to the period of starch synthesis in the tuber. Changes in activity of more than one isoform simultaneously can likewise be used to produce unique effects on amylopectin structure and hence on the properties of starch. Similarly the introduction via transformation of one or more of the isoamylases from the potato tuber into starch-synthesising organs of other species may be used to bring about unique and novel changes in the structure of amylopectin and hence in the properties of starch in those organs.

Thus in a fifth aspect of the present invention there is disclosed a host cell containing nucleic acid or a vector according to the present invention, especially a plant or a microbial cell.

This aspect of the present invention further encompasses a host cell transformed with nucleic acid or a vector according to the present invention, especially a plant or a microbial cell. Within the cell, the nucleic acid may be incorporated within the chromosome. There may be more than one such heterologous nucleotide sequence per haploid genome.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants (see below).

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (198) *Plant Tissue and Cell Culture,* Academic Press), electroporation (EP 290395, WO 8706614 Gelvin Debeyser—see attached) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1–11.

Agrobacterium transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep. 7, 379–384;* Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, Agrobacterium mediated transformation is now emerging also as an highly efficient alternative transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications,* Academic Press, 1984, and Weissbach and Weissbach, *Methods for Plant Molecular Biology,* Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Thus a sixth aspect of the present invention provides a method of generating a cell involving introduction of a vector as described in relation to the fourth aspect above into plant cell and causing or allowing recombination between the vector and the cell genome to introduce the sequence of nucleotides into the genome. Preferably the cell is a plant cell.

Thus according to the invention there is provided a plant cell having incorporated into its genome nucleic acid, particularly heterologous nucleic acid, as provided by the present invention, under operative control of a regulatory sequence for control of expression. The coding sequence may be operably linked to one or more regulatory sequences which may be heterologous or foreign to the gene i.e. which is not naturally associated with the gene for its expression. The nucleic acid according to the invention may be placed under the control of an externally inducible gene promoter to place expression under the control of the user.

The term "heterologous" may be used to indicate that the gene/sequence of nucleotides in question have been introduced into said cells of the plant or an ancestor thereof, using genetic engineering, i.e. by human intervention. A transgenic plant cell, i.e. transgenic for the nucleic acid in question, may be provided. The transgene may be on an extra-genomic vector or incorporated, preferably stably, into the genome. A heterologous gene may replace an endogenous equivalent gene, ie one which normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher or lower activity than wild-type, may be used in place of the endogenous gene. Nucleic acid heterologous, or exogenous or foreign, to a plant cell may be non-naturally occurring in cells of that type, variety or species. Thus, nucleic acid may include a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

A plant may be regenerated from one or more transformed plant cells. Thus a plant including a plant cell according to the invention forms a seventh aspect of the present invention, along with any part or propagule thereof, seed, selfed or hybrid progeny and descendants.

A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

Preferred plants of the present invention include modified potato, pea, maize, wheat, cassava, rice and barley.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant.

As discussed above, particularly embraced by the present invention are methods of influencing or affecting the starch debranching activities of a plant comprising the use of any of the nucleic acids, vectors and/or other materials or methods discussed in relation to aspects one to seven above, including causing or allowing expression of a heterologous nucleic acid sequence within cells of the plant. Such methods form an eighth aspect of the present invention.

In one embodiment there is provided a method including expression of a nucleic acid molecule having a sequence identical or complementary to all or part of Seq ID Nos 1 to 3, or a mutant, variant, allele or other derivative of the sequence, within cells of a plant (thereby producing the encoded polypeptide), following an earlier step of introduction of the nucleic acid into a cell of the plant or an ancestor thereof. Such a method may be used to influence the starch generated within the cells of that plant.

In the present invention, over-expression may be achieved by introduction of the nucleic acid molecules discussed above in a sense orientation. Thus, the present invention provides a method of influencing the starch debranching activity of a plant, the method including causing or allowing expression of the product (polypeptide or nucleic acid transcript) encoded by heterologous nucleic acid according to the invention from that nucleic acid within cells of the plant.

Conversely, down-regulation of expression of a target gene (i.e. an isoamylase encoded by any of the nucleic acid molecules of the present invention) may be achieved using anti-sense technology or "sense regulation" ("co-suppression").

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS USA* 91, 3490–3496.

An alternative is to use a copy of all or part of the target gene inserted in sense, that is the same, orientation as the target gene, to achieve reduction in expression of the target gene by co-suppression.

Both of these methods will now be discussed in more detail.

The complete sequence corresponding to the coding sequence of the targeted isoamylase (in reverse orientation for anti-sense) need not be used. For example fragments of sufficient length may be used. It is a routine matter for the person skilled in the art to screen fragments of various sizes and from various parts of the coding sequence to optimise the level of antisense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides. However it may be less, possibly about 400 nucleotides, about 300 nucleotides, about 200 nucleotides, or about 100 nucleotides. It may be even be possible to use oligonucleotides of much shorter lengths, 14–23 nucleotides. Longer fragments, for instance longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene, although it may be advantageous to have minimal mismatch.

Thus generally speaking, the transcribed nucleic acid may represent a fragment of an isoamylase gene, such as any one of those corresponding to Seq ID Nos 1 to 3, or the complement thereof, or may be a mutant, derivative, variant or allele thereof, in similar terms as discussed above in relation to alterations being made to an coding sequence and the homology of the altered sequence (see the first or second aspects of the invention). The homology may be sufficient for the transcribed anti-sense RNA to hybridise with nucleic acid within cells of the plant, though irrespective of whether hybridisation takes place the de sired effect is down-regulation of gene expression.

Anti-sense regulation may itself be regulated by employing an inducible promoter in an appropriate construct. Thus, the present invention also provides a method of influencing a starch debranching activity of a plant, the method including causing or allowing anti-sense transcription from heterologous nucleic acid according to the invention within cells of the plant.

The anti-sense constructs (nucleic acids) themselves are also embraced by the present invention, as is use of these constructs for down-regulation of gene expression, particularly down-regulation of expression of an isoamylase or homologue thereof, preferably in order to influence the starch debranching enzyme activity of a plant, especially a crop plant.

As discussed above, when additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is well-reported in scientific and patent literature and is used routinely for gene control. See, for example, van der Krol et al., (1990) *The Plant Cell* 2, 291–229; Napoli et al., (1990) The Plant Cell 2, 279–289; Zhang et al, 1992 *The Plant Cell* 4, 1575–1588, and U.S. Pat. No. 5,231,020.

Again, anti-sense fragments, mutants and so on may be used in similar terms as described above in relation to the second aspect.

Further methods of down-regulating activity include inhibition by expressing dominant negative versions (i.e. mutant or truncated versions) of the isoamylases which will inhibit endogenous, wild-type enzymes in a competitive or non-competitive way e.g. by competing for binding sites on the starch granules, or by association to form non-functional multimers. Alternatively one can use ribozymes, e.g. hammerhead ribozymes, which can catalyse the site-specific cleavage of RNA, such as mRNA (see e.g. Jaeger (1997) "The new world of ribozymes" Curr Opin Struct Biol 7:324–335, or Gibson & Shillitoe (1997) "Ribozymes: their functions and strategies form their use" Mol Biotechnol 7: 242–251.)

Thus, the present invention also provides a method of influencing a starch debranching activity of a plant, the method including causing or allowing transcription of nucleic acid as described above, within cells of the plant.

Here the starch debranching activity of the produce is preferably suppressed as a result of under-expression of isoamylase within the plant cells.

In a ninth aspect of the invention there is disclosed the expression product (preferably being an isoamylase) of any of the nucleic acid sequences disclosed above, particularly those of the first and second aspects of the invention, optionally by means of the vectors of the fourth aspect. Example amino acid sequences are given in FIGS. 4 to 6. Also embraced are methods of generating isoamylases by expression from encoding nucleic acid therefore under suitable conditions, which may be in suitable host cells. Following expression, the product may be isolated from the expression system and may be used as desired, for instance in formulation of a composition including at least one additional component.

One particular use for such expression products may be raising antibodies. Such antibodies form a tenth aspect of the present invention.

Thus purified protein of the ninth aspect, or a fragment, mutant, derivative or variant thereof, e.g. produced recombinantly by expression from encoding nucleic acid, may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used, inter alia, in the identification and/or isolation and/or localisation (e.g. intracellular) of the peptides of the present invention and homologous polypeptides, and may also permit isolation of the encoding genes. Thus, the present invention provides a method of identifying or isolating a polypeptide with starch debranching function (in accordance with embodiments disclosed herein), comprising screening candidate polypeptides with a polypeptide comprising the antigen-binding domain of an antibody (for example whole antibody or a fragment thereof) which is able to bind an starch debranching polypeptide or fragment, variant or derivative thereof or preferably has binding specificity for such a polypeptide. Specific binding members such as antibodies and polypeptides comprising antigen binding domains of antibodies that bind and are preferably specific for an isoamylase or mutant, variant or derivative thereof represent further aspects of the present invention, as do their use and methods which employ them.

Candidate polypeptides for screening may for instance be the products of an expression library created using nucleic acid derived from an plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases, as discussed above.

An eleventh aspect of the present invention is a polysaccharide generated (in vivo or using an enzyme preparation) by a process comprising the use of an isoamylase of the ninth aspect. Also embraced is starch produced in the transformed plants and cells discussed above. Such starch is preferably derived from amylopectin but has any of a decreased, increased or otherwise altered degree of branching, with a corresponding alteration in properties e.g. swelling or ability to form a paste rather than a gel when heated in water. Commodities (e.g. foodstuffs) comprising such starches form a further aspect of the present invention.

Other commodities which may benefit from the modified starches of the present invention include biodegradable plastics; food-processing thickeners; starch coated films, papers & textiles; paint thickeners; mining explosives; pharmaceuticals and glues. The modified starches can be used analagously to prior art starches in these materials, in ways which are well known to those skilled in the respective technical fields.

The invention will now be further illustrated with reference to the following non-limiting Figures and Examples. Other embodiments falling within the scope or the invention will occur to those skilled in the art in the light of these.

BRIEF DESCRIPTION OF THE FIGURES

FIGS. 1a and 1b show nucleotide Seq ID No 1 (from isoamylase clone 21).

FIGS. 2a and 2b show nucleotide Seq ID No 2 (from isoamylase clone 15).

FIGS. 3a and 3b show nucleotide Seq ID No 3 (from isomylase clone 9).

FIG. 4 shows amino acid Seq ID No 4 (from isoamylase clone 21).

FIG. 5 show amino acid Seq ID No 5 (from isoamylase clone 15).

FIG. 6 show amino acid Seq ID No 6 (from isomylase clone 9).

FIG. 7 shows Seq ID No 7, corresponding to the Arabidopsis thaliana v. columbia probe At69012.new_est taken from the Medline Database, originally published by Newman et al (1994) Plant Physiol 106: 1241–1255.

FIGS. 8A–8B. FIG. 8(a) shows the transit peptide sequence from clone 21 (Seq ID No 8). FIG. 8(b) shows the transit peptide sequence from clone 15 (Seq ID No 9).

FIGS. 10a and 10b show nucleotide Seq ID No 10 (original sequence from isoamylase clone 21).

FIGS. 11a and 11b show nucleotide Seq ID No 11 (original sequence from isoamylase clone 15).

FIG. 12 shows nucleoside Seq ID No 12 (original sequence from isomylase clone 9).

FIG. 13 shows amino acid Seq ID No 13 (original sequence from isoamylase clone 21).

FIG. 14 shows amino acid Seq ID No 14 (original sequence from isoamylase clone 15). 'x' is unknown aminoacid. '*' is a stop codon.

FIG. 15 shows amino acid Seq ID No 15 (original sequence from isomylase clone 9).

FIGS. 16A–16B. FIG. 16(a) shows the forward primer (Seq ID No 16) used to isolate the probe (see Examples below). FIG. 16(b) shows the reverse primer (Seq ID No 17).

DETAILED DESCRIPTION OF THE INVENTION

EXAMPLES

Example 1

Figure 9:
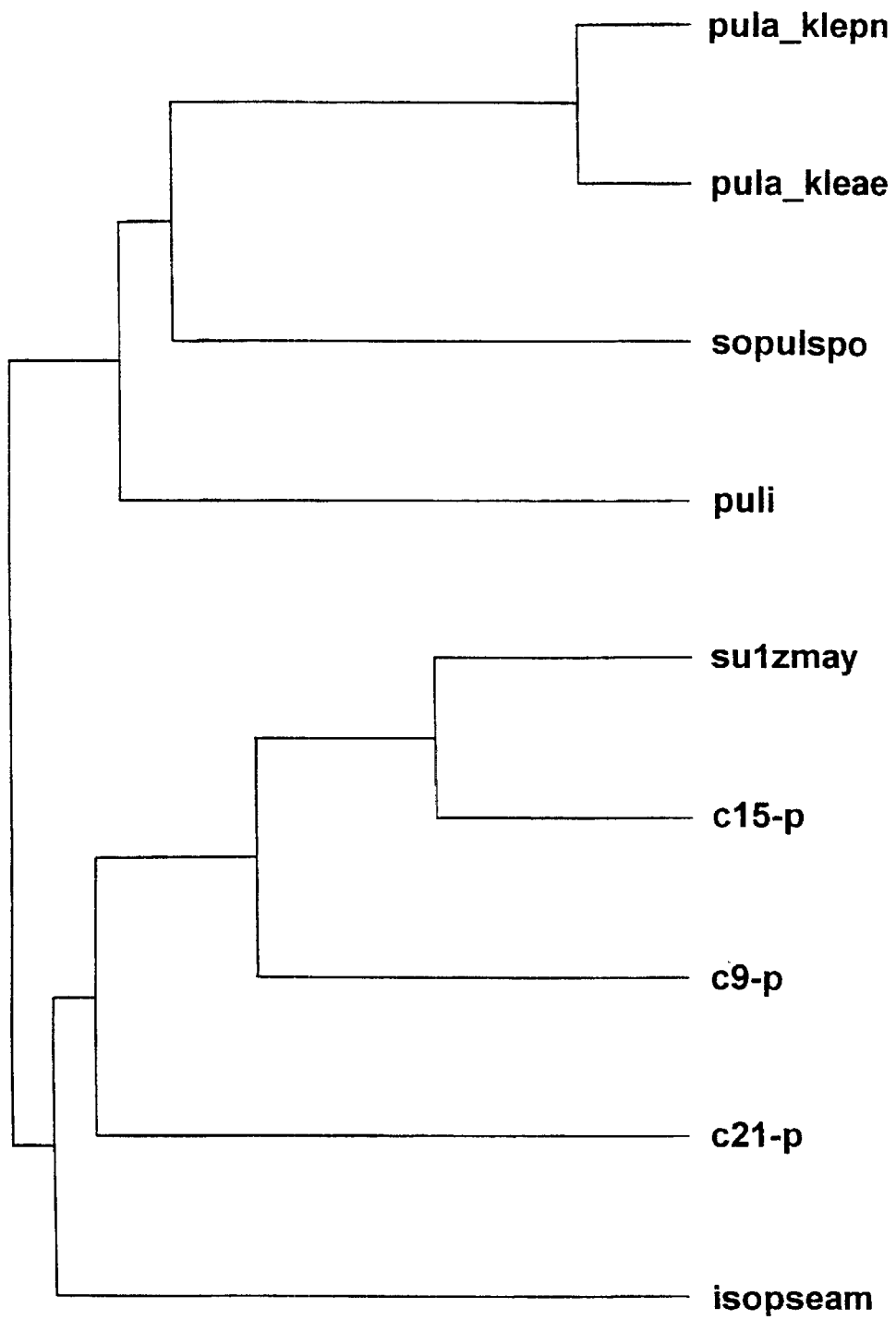
FIG. 9 shows a dendogram which places the debranching enzymes in 2 distinct groups, with clones 15, 9 and 21 all aligning with the isoamylases.

Cloning of the Debranchina Enzymes from Potato

Briefly, cDNA clones from potato were isolated from cDNA libraries synthesised from mRNA from both developing tubers and from in vitro grown minitubers. The probe was an EST from Arabidopsis (At69012.new_est) which was identified by the present inventors as showing significant homology to the su1 gene from maize.

Libraries

Two independent libraries were prepared. These were
a) from mRNA from developing tubers from greenhouse cultivated potato plants (*Solanum tuberosum* var *desiree*)
b) from mRNA from minitubers indued on stem explants of potato (*Solanum tuberosum* var *desiree*) cultured in vitro according to the method of Visser et al (1994) Physiol Plantarum 90: 285–292. Minitubers were used in addition to tubers in order to assess starch synthesising organ which has a different gene express ion profile to tubers.

The CDNA was synthesized by reverse transcription using as a template poly(A)RNA passed twice over oligo (dT)cellulose. The poly(A)RNA was reverse transcribed to form the first strand CDNA and the second strand was prepared using DNA polymerase I (large subunit), T4 DNA polymerase and RNAase H as described in the manufacturer's instructions for the cDNA synthesis kit (Amersham plc, UK).

cDNA was ligated to EcoRI adaptors as described in the Rapid adapter ligation kit (Amersham plc, UK) and then cloned into the EcoRI of the λ cloning vector λgt10 according to the manufacturers instructions for the λgt10 cloning kit (Amersham plc, UK).

Probe

The probe used was a fragment of an Arabidopsis EST (EMBL ID No. At69012.new_est; accession no. H36690). This EST was identified initially using a BLAST search of EST databases.

In order to determine the extent of the homology between the Arabidopsis EST and the Su1 gene product, the EST was further sequenced using an Applied Biosystems Taq cycle sequencing kit (Perkin Elmer) and an ABI automated sequencer. This generated a further 780 bp sequence data. It showed significant homology to the deduced amino acid sequence for the product of the Su1 gene from maize that encodes an isoamylase type of debranching enzyme.

The probe was prepared using PCR amplification of a miniprep of the plasmid. The PCR used the M13 reverse primer:

5'-CAG GAA ACA GCT ATG AC-3' (SEq ID No 5)

And also a primer specific for the 3' end of the EST, at a point before the polyA tail. This was designated G3712:

5'-GAT CAT AAC TTG AGT TCT AAG CGG-3'

The amplified fragment was cut with PstI to remove the sequences from the vector. The fragment was purified and then labelled using an oligonucleotide random priming labelling kit to provide the probe.

Screening

Approximately 60,000 plaques from the tuber library (unamplified) and 60,000 plaques from the minituber library (unamplified) were used to infect *E. coli* (strain NM514) and the resultant plaques were screened using a 1.2 kb fragment of EST cDNA clone (At69012.new_est) which lacked the poly(A) tail. Filters were subsequently washed at low stringency (2×SSC, 0.5%SDS, 55° C. for two washes).

16 independent phages (5 from tuber and 11 from minituber) that showed different levels of hybridization to the EST probe were selected.

Subcloning

DNA from 9 independent clones was subcloned into either pCR2.1 (Invitrogen) or pBluescript (Stratagene) in *E. coli*. Those in pCR2.1 were subcloned following PCR amplification of the inserts using λAgt10 specific oligonucleotides. Those in pBluescript were isolated as EcoRI fragments from λDNA preparations.

Sequencing & Analysis

Clones were sequenced using the Taq cycle sequencing kit from Perkin Elmer and the ABI automated sequencer. To complete any incomplete sequence, primers based on the known portions of the sequence are used to 'walk' along the clones in the library to identify the remaining portions. Following initial sequencing of the C9 clone, a longer cDNA was obtained and sequenced.

The predicted N-terminal amino acid sequences for C15 and C21 fit the criteria for plastid transit peptides. A summary of the cDNA clones is presented below. This refers to the original sequences. Corresponding comparisons with Su1 for the new sequences are shown above.

TABLE 3

| cDNA clones | length (kb) | open reading frame (number of amino acids) | | relationship to sul (%, at amino acid level) | |
|---|---|---|---|---|---|
| | | total | predicted transit peptide | similarity | identity |
| C9 | 2.6 | 766 | none | 61 | 45 |
| C15 | 2.7 | 793 | 47 | 82 | 70 |
| C21 | 2.9 | 878 | 38 | 57 | 35 |

Example 2

Transformation and Antisense Constructs

The clones encoding the isoamylases are used to construct a series of lines of antisense potato plants. The clone (C9, C15 and C21) is subcloned in antisense orientation between the CaMV 35S promoter and the CaMV terminator sequences of pJIT60 (see Guerineau & Mullinieaux (1993) in Plant Molecular Biology Lab Fax ed. Croy RRD BIOS Scientific, Oxford, UK pp 121–148). This construct has been subcloned into the primary vector pBin19 and transferred to *Agrobacterium tumifaciens* (LBA4404) by transformation and from there to potato tuber discs by the method of Spychalla and Bevan (1993) Plant Tissue Culture Manual BII.

Example 3

Transformation and Overexpression Constructs

In other transformants, full length cDNA clones encoding the isoamylase type of debranching enzyme in potato are used to increase debranching enzyme activity levels in transgenic potatoes. This is achieved by cloning each of them between the 2×CaMV 35S promoter and the CaMV Terminator of pJIT60. Thence into a binary vector such as pBin19 between the T-DNA borders in *E. coli*. It is then transferred to *Agrobacterium tumifaciens* for transformation into plants.

Example 4

Enzyme Purification

Each different cDNA may be expressed in *E. coli* to define its activity closely and to obtain enough purified protein to produce an antiserum. This could be done using any suitable system e.g. the pSTAG expression vector for E. coli (strain K38) (Moyano et al (1996) Plant Cell 8: 1519–1532):

All three cDNA's were inserted into a vector which permitted expression in E.coli of proteins fused to a 15 amino acid tag at the N-terminus (pET Expression system, Novagen). The amount of expressed protein in E.coli extracts was then quantified by an assay for the S-tag and the proteins were then purified on an affinity matrix specific for the S-tag, The C21 and C15 cDNA's were inserted into the vector after removal of the fragment encoding the putative transit peptide (pET system manual 7th Edition, Novagen).

Fusion proteins from the C15 and C21 cDNA's were successfully expressed to high levels in E.Coli as determined by using SDS-polyacrylamide gels (not shown). In both cases, single bands of protein not present in E.coli transformed with the vector alone are seen in crude extracts of both the soluble and unsoluble (inclusion body) fractions of the bacteria. These bands correspond closely in size to the predicted size for the expressed proteins: 87 kD for C15 and 97 kD for C21.

The recombinant isoamylase is most readily assayed when it is either purified from other hydrolases or by use of specific inhibitors to negate the contribution of interfering enzymes. It may also be visualized on non-denaturing glucan-containing polyacrylamide gels on which activities of starch hydrolozing enzymes are separated and then revealed by staining of hydrolysis products with iodine (see Kakefuda et al. 1986 Planta 168: 175–182.

Example 5

Preparation of Antisera

Polyclonal antibodies against C15 and C21 were produced in New Zealand white rabbits using standard immunisation procedures (Harlow E. & Land D. (1988) Antibodies: A Laboratory Manual, Cold Spring Harbor Laboratory Press, Cold Spring Harbour, N.Y).

The immunoblot analysis was performed according to standard procedures (Sambrook J et al (1989) Molecular Cloning: A Laboratory Manual, Cold Spring harbor Laboratory Press, Cold Spring Harbor, N.Y.). Filters were incubated with the rabbit antiserum and immunoreactive bands were detected using the methods of Towbin H. Et al (1997) Proc. Natl. Acad. Sci. USA 76: 4350–4354.

The presence of high-titer antibodies in antisera that recognised the proteins was demonstrated by immunoblot analysis of extracts from E.coli expressing eiher C15 or C21. Both C15 and C21 antisera immunoreact against C15 and C21.

LITERATURE CITED

Ball et al (1996) Cell 86, 349–352.
James et al (1995) Plant Cell 7, 417–429.
Mouille et al (1996) Plant Cell 8, 1353–1356.
Nakamura et al (1996a) Physiol. Plant 97, 491–498.
Nakamura et al (1996b) Planta 199, 209–218.
Pan and Nelson (1984) Plant Physiol. 74, 324–328.

What is claimed is:

1. An isolated nucleic acid which comprises a nucleotide sequence which:
   (a) encodes a polypeptide which is an isoamylase and is selected from the group consisting of polypeptides having the amino acid sequence shown in SEQ ID NOS: 4, 5 and 6; and
   (b) is obtainable from *Solanum tuberosum*.

2. An isolated nucleic acid comprising a nucleotide sequence encoding an isoamylase, wherein the sequence: (a) consists of any one of SEQ ID NOS: 1, 2, or 3 or (b) is degeneratively equivalent to any one of SEQ ID NOS: 1, 2, or 3, or (c) is a homologous variant of SEQ ID NOS: 1, 2 or 3, sharing at least 85% sequence identity with any of said sequences, wherein the variant is either: an allelic variant of SEQ ID NOS: 1, 2, or 3, or a derivative of SEQ ID NOS: 1, 2, or 3 by way of one or more of addition, insertion, deletion or substitution of one or more nucleotides.

3. A nucleic acid which is complementary to the nucleic acid of claim 2.

4. A recombinant vector comprising the nucleic acid of claim 2, which vector is capable of replicating in a suitable host.

5. A vector as claimed in claim 4, wherein the nucleic acid is operably linked to a promoter or other regulatory element for transcription in a host cell, which vector further comprises any one or more of the following: a terminator sequence; a polyadenylation sequence; an enhancer sequence; and a marker gene.

6. A method comprising the step of introducing a vector as claimed in claim 4 into a plant cell.

7. A method for transforming a plant cell, comprising a method as claimed in claim 6, and further comprising the step of causing or allowing recombination between the vector and the plant cell genome to introduce the nucleic acid into the genome.

8. A plant host cell transformed with a vector as claimed in claim 4.

9. A method for producing a transgenic plant, which method comprises a method as claimed in claim 7 and further comprises the step of regenerating a plant from the transformed cell.

10. A plant comprising the cell of claim 8.

11. A plant as claimed in claim 10 produced by (i) introducing into a plant cell, a recombinant vector comprising an isolated nucleic acid having a nucleotide sequence encoding an isoamylase, wherein the sequence: (a) consists of any one of SEQ ID NO: 1, 2, or 3 or (b) is degeneratively equivalent to any one of SEQ ID NOS: 1, 2, or 3, or (c) is a homologous variant of SEQ ID NOS: 1, 2, or 3, sharing at least 85% sequence identity with any of said sequences, wherein the variant is either: an allelic variant of SEQ ID NOS: 1, 2, or 3, or a derivative of SEQ ID NOS: 1, 2, or 3 by way of one or more of addition, insertion, deletion or substitution of one or more nucleotides, said vector being capable of replicating in said plant cell, (ii) causing or allowing recombination between the vector and the plant cell genome to introduce the nucleic acid into the genome and (iii) regenerating a plant from the transformed cell.

12. A plant which is the progeny of a plant as claimed in claim 11.

13. A plant as claimed in claim 11 which is selected from the group consisting of: potato; pea; maize; wheat; cassava; rice and barley.

14. A part or a propagule of the plant of claim 11.

15. A method of producing a polypeptide comprising the step of causing or allowing the expression from a heterologous nucleic acid of claim 2 in a suitable host cell.

16. A method for altering the quality or quantity of a polysaccharide in a host cell by influencing the isoamylase activity in that cell, the method comprising the step of causing or allowing expression of a heterologous nucleic acid according to claim 2 within the cell.

17. A method as claimed in claim 16 wherein the subcellular location of the isoamylase activity is manipulated.

18. A method as claimed in claim 16, wherein the activity of two or more isoamylases is manipulated.

19. A method as claimed in claim 16 wherein the polysaccharide is amylopectin.

20. A method as claimed in claim 19 wherein the quality altered is the branching of the amylopectin, and the amylopectin is altered in at least one of the following ways:
(a) the degree of branching is decreased, or
(b) the degree of branching is increased, or
(c) the branching pattern is changed.

\* \* \* \* \*